(12) United States Patent
Karve et al.

(10) Patent No.: US 12,144,871 B2
(45) Date of Patent: Nov. 19, 2024

(54) STABLE COMPOSITIONS OF MRNA-LOADED LIPID NANOPARTICLES AND PROCESSES OF MAKING

(71) Applicant: Translate Bio, Inc., Lexington, MA (US)

(72) Inventors: Shrirang Karve, Lexington, MA (US); Frank DeRosa, Lexington, MA (US); Michael Heartlein, Lexington, MA (US); Natalia Vargas Montoya, Lexington, MA (US); Priyal Patel, Lexington, MA (US); Ashish Sarode, Lexington, MA (US)

(73) Assignee: TRANSLATE BIO, INC., Lexington, MA (US)

( * ) Notice: Subject to any disclaimer, the term of this patent is extended or adjusted under 35 U.S.C. 154(b) by 0 days.

(21) Appl. No.: 16/936,909

(22) Filed: Jul. 23, 2020

(65) Prior Publication Data

US 2021/0046192 A1    Feb. 18, 2021

Related U.S. Application Data

(60) Provisional application No. 62/877,597, filed on Jul. 23, 2019.

(51) Int. Cl.
| | | |
|---|---|---|
| A61K 48/00 | (2006.01) | |
| A61K 9/107 | (2006.01) | |
| A61K 47/32 | (2006.01) | |
| A61K 47/34 | (2017.01) | |

(52) U.S. Cl.
CPC .......... *A61K 48/005* (2013.01); *A61K 9/1075* (2013.01); *A61K 47/32* (2013.01); *A61K 47/34* (2013.01); *A61K 48/0041* (2013.01)

(58) Field of Classification Search
CPC .... A61K 48/005; A61K 9/1075; A61K 47/32; A61K 47/34; A61K 48/0041; C12N 15/88
See application file for complete search history.

(56) References Cited

U.S. PATENT DOCUMENTS

2017/0281542 A1* 10/2017 Heartlein ............ A61K 9/1272
2018/0207319 A1*  7/2018 Eslahi .................. A61L 27/52

FOREIGN PATENT DOCUMENTS

| RU | 2649364 C2 | 4/2018 | |
|---|---|---|---|
| WO | WO 2017/218704 A1 | 12/2017 | |
| WO | WO 2018/089540 A1 | 5/2018 | |
| WO | WO-2019126783 A1 * | 6/2019 | ......... A61K 31/4535 |
| WO | WO 2019/207060 A1 | 10/2019 | |

OTHER PUBLICATIONS

Ahmed et al., Int'l J Pharmaceuticals 567 (2019) 118488. (Year: 2019).*
Ahmed et al., "Conception of nanosized hybrid/poloxamer particles to thicken the interior core of liposomes and delay hydrophilic drug delivery," Int'l Pharmaceuticals 567 (2019) 118488. (Year: 2019). 11 pages.
Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, vol. 3, Issue 5, (2016). 240 pages.
International Search Report and Written Opinion for PCT/US20/43223, dated Nov. 5, 2020. 9 pages.
Hajj et al., "Branched-Tail Lipid Nanoparticles Potently Deliver mRNA In Vivo due to Enhanced Ionization at Endosomal pH," Small, 2019, vol. 15, Article 1805097, 7 pages.
Official Action and Search Report for related Russian Patent Application No. 2022104357 issued May 21, 2024, 17 pages including English Translation.

* cited by examiner

*Primary Examiner* — Robert S Cabral
(74) *Attorney, Agent, or Firm* — MH2 Technology Law Group, LLP

(57) ABSTRACT

The present invention provides an improved compositions and processes for preparing mRNA-loaded lipid nanoparticles (mRNA-LNPs). In some embodiments, the present invention provides mRNA-LNPs with exceptional stability and is particularly useful in cases where LNPs comprising low or no PEG-modified lipids are desired.

16 Claims, 7 Drawing Sheets

STABLE COMPOSITIONS OF MRNA-LOADED LIPID NANOPARTICLES AND PROCESSES OF MAKING

CROSS-REFERENCE TO RELATED APPLICATIONS

The present application claims priority to U.S. Provisional Application Ser. No. 62/877,597 filed Jul. 23, 2019, the disclosures of which are hereby incorporated by reference.

BACKGROUND

Messenger RNA therapy (MRT) is becoming an increasingly important approach for the treatment of a variety of diseases. MRT involves administration of messenger RNA (mRNA) to a patient in need of the therapy for production of the protein encoded by the mRNA within the patient's body. Lipid nanoparticles are commonly used to encapsulate mRNA for efficient in vivo delivery of mRNA.

Much effort has been made on developing improved methods and compositions that can enhance in vivo delivery and/or expression of mRNA using lipid nanoparticles, which can be adapted to a scalable and cost-effective manufacturing process. At the same time, it is important that any such enhancements to in vivo delivery and/or expression of mRNA also maintain or improve upon the safety and tolerability of the compositions associated with lipid mediated mRNA delivery.

SUMMARY OF THE INVENTION

The present invention provides, among other things, further improved compositions and processes for preparing mRNA-loaded lipid nanoparticles (mRNA-LNPs). Prior to the present invention, PEG-modified lipids typically were included in lipid nanoparticle (LNP) formulations as they were known to increase shelf stability and in vivo circulating time. On the other hand, PEG-modified lipids may induce accelerated blood clearance (ABC) and/or innate immune response by, among other things, producing anti-PEG antibodies. To address this issue, attempts have been made to prepare mRNA-LNPs without PEG-modified lipids. However, it has been observed that mRNA-loaded LNPs formed in the absence of PEG-modified lipids or PEG have large and unstable sizes, particularly after freeze and thaw, or tend to precipitate, rendering them unsuitable for therapeutic use. The present invention is, in part, based on the surprising discovery that unexpectedly stable mRNA-loaded LNPs with low or no PEG-modified lipids can be made by mixing the mRNA and lipids in the presence of amphiphilic block copolymer such as poloxamer. As described in more detail below, mRNA-LNPs made according to the present invention have sizes comparable to those conventional LNPs containing a typical amount of PEG-modified lipids and more importantly, are stable following one or more freeze thaw cycles. In particular, the mRNA-LNPs according to the present invention maintain an average diameter within 50%, and in some cases, within 10% of the original average size following one or more freeze thaw cycles. Moreover, poloxamer shielded LNPs with low or no PEG-modified lipids (e.g., <0.5% PEG-modified lipids) achieved in vivo protein expression profile similar to conventional LNPs (e.g., those with 5% PEG-modified lipids). Thus, the present invention provides further improved mRNA-LNPs with exceptional stability and is particularly useful in cases where LNPs comprising low or no PEG-modified lipids are desired, for example, to avoid generating anti-PEG antibodies, and/or ABC.

In one aspect, the present invention provides a stable composition comprising lipid nanoparticles encapsulating messenger RNA (mRNA) encoding a protein or a peptide, wherein each of the lipid nanoparticles comprises one or more cationic lipids and less than 0.5% of PEG-modified lipids or PEG and is stable following one or more freeze thaws. In some embodiments, the lipid nanoparticles further comprise one or more non-cationic lipids.

In some embodiments, the lipid nanoparticles comprise a cationic lipid, dioleoylphosphatidylethanolamine (DOPE) as the non-cationic lipid, and less than about 0.5% of PEG-modified lipids or PEG. In some embodiments, the lipid nanoparticles comprise a cationic lipid, 1,2-Dierucoyl-sn-glycero-3-phosphoethanolamine (DEPE) as the non-cationic lipid, and less than about 0.5% of PEG-modified lipids or PEG.

In some embodiments, the lipid nanoparticles encapsulating the mRNA maintain an average diameter within 50% of the original average size following one or more freeze thaw cycles. In some embodiments, the lipid nanoparticles encapsulating the mRNA maintain an average diameter within 40% of the original average size following one or more freeze thaw cycles. In some embodiments, the lipid nanoparticles encapsulating the mRNA maintain an average diameter within 30% of the original average size following one or more freeze thaw cycles. In some embodiments, the lipid nanoparticles encapsulating the mRNA maintain an average diameter within 20% of the original average size following one or more freeze thaw cycles. In some embodiments, the lipid nanoparticles encapsulating the mRNA maintain an average diameter within 10% of the original average size following one or more freeze thaw cycles. In some embodiments, the lipid nanoparticles encapsulating the mRNA maintain an average diameter within 5% of the original average size following one or more freeze thaw cycles.

In some embodiments, the lipid nanoparticles have an mRNA encapsulation efficiency of between about 50% and 99%. In some embodiments, the lipid nanoparticles have an mRNA encapsulation efficiency of between about 60% and 90%. In some embodiments, the lipid nanoparticles have an mRNA encapsulation efficiency of about 60%. In some embodiments, the lipid nanoparticles have an mRNA encapsulation efficiency of about 70%. In some embodiments, the lipid nanoparticles have an mRNA encapsulation efficiency of about 80%. In some embodiments, the lipid nanoparticles have an mRNA encapsulation efficiency of about 90%.

In some embodiments, each of the lipid nanoparticles further comprises a cholesterol-based lipid.

In some embodiments, each of the lipid nanoparticle comprises 0.4% of PEG-modified lipids or less. In some embodiments, each of the lipid nanoparticle comprises 0.3% of PEG-modified lipids or less. In some embodiments, each of the lipid nanoparticle comprises 0.2% of PEG-modified lipids or less. In some embodiments, each of the lipid nanoparticle comprises 0.1% of PEG-modified lipids or less.

In some embodiments, each of the lipid nanoparticle is substantially free of PEG-modified lipids.

In some embodiments, each of the lipid nanoparticle comprises an amphiphilic block copolymer.

In some embodiments, each of the lipid nanoparticles comprises less than 3% amphiphilic block copolymer. In some embodiments, each of the lipid nanoparticles comprises less than 3% amphiphilic block copolymer. In some embodiments, each of the lipid nanoparticles comprises less than 2.5% amphiphilic block copolymer. In some embodiments, each of the lipid nanoparticles comprises less than 2% amphiphilic block copolymer. In some embodiments, each of the lipid nanoparticles comprises less than 1.5% amphiphilic block copolymer. In some embodiments, each of the lipid nanoparticles comprises less than 1% amphiphilic block copolymer. In some embodiments, each of the lipid nanoparticles comprises less than 0.5% amphiphilic block copolymer. In some embodiments, each of the lipid nanoparticles comprises less than 0.05% amphiphilic block copolymer. In some embodiments, each of the lipid nanoparticles comprises less than 0.01% amphiphilic block copolymer.

In some embodiments, the composition comprises less than 0.05% amphiphilic block copolymer of the total composition by weight. In some embodiments, the composition comprises less than 0.04% amphiphilic block copolymer of the total composition by weight. In some embodiments, the composition comprises less than 0.03% amphiphilic block copolymer of the total composition by weight. In some embodiments, the composition comprises less than 0.02% amphiphilic block copolymer of the total composition by weight. In some embodiments, the composition comprises less than 0.01% amphiphilic block copolymer of the total composition by weight.

In some embodiments, the composition comprises a residual of amphiphilic block copolymer.

In some embodiments, a suitable amphiphilic block copolymer is a poloxamer.

In some embodiments, a suitable poloxamer is poloxamer 84. In some embodiments, a suitable poloxamer is poloxamer 101. In some embodiments, a suitable poloxamer is poloxamer 105. In some embodiments, a suitable poloxamer is poloxamer 108. In some embodiments, a suitable poloxamer is poloxamer 122. In some embodiments, t a suitable poloxamer is poloxamer 123. In some embodiments, a suitable poloxamer is poloxamer 124. In some embodiments, a suitable poloxamer is poloxamer 181. In some embodiments, a suitable poloxamer is poloxamer 182. In some embodiments, a suitable poloxamer is poloxamer 183. In some embodiments, a suitable poloxamer is poloxamer 184. In some embodiments, a suitable poloxamer is poloxamer 185. In some embodiments, a suitable poloxamer is poloxamer 188. In some embodiments, a suitable poloxamer is poloxamer 212. In some embodiments, a suitable poloxamer is poloxamer 215. In some embodiments, a suitable poloxamer is poloxamer 217. In some embodiments, a suitable poloxamer is poloxamer 231. In some embodiments, a suitable poloxamer is poloxamer 234. In some embodiments, a suitable poloxamer is poloxamer 235. In some embodiments, a suitable poloxamer is poloxamer 237. In some embodiments, a suitable poloxamer is poloxamer 238. In some embodiments, a suitable poloxamer is poloxamer 282. In some embodiments, a suitable poloxamer is poloxamer 284. In some embodiments, a suitable poloxamer is poloxamer 288. In some embodiments, a suitable poloxamer is poloxamer 304. In some embodiments, a suitable poloxamer is poloxamer 331. In some embodiments, a suitable poloxamer is poloxamer 333. In some embodiments, a suitable poloxamer is poloxamer 334. In some embodiments, a suitable poloxamer is poloxamer 335. In some embodiments, a suitable poloxamer is poloxamer 338. In some embodiments, a suitable poloxamer is poloxamer 401. In some embodiments, a suitable poloxamer is poloxamer 402. In some embodiments, a suitable poloxamer is poloxamer 403. In some embodiments, a suitable poloxamer is poloxamer 407. In some embodiments, a suitable poloxamer is a combination thereof.

In one aspect, the present invention provides a stable composition comprising lipid nanoparticles encapsulating a messenger RNA (mRNA) that encodes a protein or a peptide, wherein each of the lipid nanoparticles comprises one or more cationic lipids, one or more non-cationic lipids, a poloxamer and is substantially free of PEG-modified lipids or PEG, and wherein the lipid nanoparticles encapsulating the mRNA are stable following one or more freeze thaw cycles.

In one aspect, the present invention provides a stable composition comprising lipid nanoparticles encapsulating a messenger RNA (mRNA) that encodes a protein or a peptide, wherein each of the lipid nanoparticles comprises one or more cationic lipids, one or more non-cationic lipids, a poloxamer and is substantially free of PEG-modified lipids or PEG, and wherein the lipid nanoparticles encapsulating the mRNA generate low to no anti-PEG antibodies, and/or reduce accelerated blood clearance (ABC).

In some embodiments, the poloxamer is present in the lipid nanoparticles at an amount of less than 0.1%. In some embodiments, the poloxamer is present in the lipid nanoparticles at an amount of less than 0.05%.

In some embodiments, a suitable non-cationic lipid is dioleoylphosphatidylethanolamine (DOPE). In some embodiments, a suitable non-cationic lipid is 1,2-Dierucoyl-sn-glycero-3-phosphoethanolamine (DEPE).

In some embodiments, each of the lipid nanoparticles does not comprise a cholesterol-based lipid.

In some embodiments, each of the lipid nanoparticles is a two-component lipid nanoparticles.

In some embodiments, a suitable poloxamer has ethylene oxide units from about 10 to about 150.

In some embodiments, a suitable poloxamer has propylene oxide units from about 10 to about 100.

In some embodiments, a suitable poloxamer has an average molecular weight of about 4,000 g/mol to about 20,000 g/mol. In some embodiments, a suitable poloxamer has an average molecular weight of about 1,000 g/mol to about 50,000 g/mol. In some embodiments, a suitable poloxamer has an average molecular weight of about 1,000 g/mol. In some embodiments, a suitable poloxamer has an average molecular weight of about 2,000 g/mol. In some embodiments, a suitable poloxamer has an average molecular weight of about 3,000 g/mol. In some embodiments, a suitable poloxamer has an average molecular weight of about 4,000 g/mol. In some embodiments, a suitable poloxamer has an average molecular weight of about 5,000 g/mol. In some embodiments, a suitable poloxamer has an average molecular weight of about 6,000 g/mol. In some embodiments, a suitable poloxamer has an average molecular weight of about 7,000 g/mol. In some embodiments, a suitable poloxamer has an average molecular weight of about 8,000 g/mol. In some embodiments, a suitable poloxamer has an average molecular weight of about 9,000 g/mol. In some embodiments, a suitable poloxamer has an average molecular weight of about 10,000 g/mol. In some embodiments, a suitable poloxamer has an average molecular weight of about 20,000 g/mol. In some embodiments, a suitable poloxamer has an average molecular weight of about 25,000 g/mol. In some embodiments, a suitable poloxamer has an average molecular weight of about 30,000 g/mol. In some embodiments, a suitable poloxamer has an average molecular weight of about 40,000 g/mol. In some embodiments, a suitable poloxamer has an average molecular weight of about 50,000 g/mol.

In some embodiments, the lipid nanoparticles have an average size of less than about 250 nm. In some embodiments, the lipid nanoparticles have an average size of about 200 nm or less. In some embodiments, the lipid nanoparticles have an average size of about 180 nm or less. In some embodiments, the lipid nanoparticles have an average size of about 160 nm or less. In some embodiments, the lipid nanoparticles have an average size of about 150 nm or less. In some embodiments, the lipid nanoparticles have an average size of about 140 nm or less. In some embodiments, the lipid nanoparticles have an average size of about 130 nm or less. In some embodiments, the lipid nanoparticles have an average size of about 120 nm or less. In some embodiments, the lipid nanoparticles have an average size of about 110 nm or less. In some embodiments, the lipid nanoparticles have an average size of about 100 nm or less.

In some embodiments, the lipid nanoparticles have a polydispersity index (PDI) of 0.3 or less. In some embodiments, the lipid nanoparticles have a polydispersity index (PDI) of 0.25 or less. In some embodiments, the lipid nanoparticles have a polydispersity index (PDI) of 0.20 or less. In some embodiments, the lipid nanoparticles have a polydispersity index (PDI) of 0.18 or less. In some embodiments, the lipid nanoparticles have a polydispersity index (PDI) of 0.17 or less. In some embodiments, the lipid nanoparticles have a polydispersity index (PDI) of 0.16 or less. In some embodiments, the lipid nanoparticles have a polydispersity index (PDI) of 0.15 or less. In some embodiments, the lipid nanoparticles have a polydispersity index (PDI) of 0.14 or less. In some embodiments, the lipid nanoparticles have a polydispersity index (PDI) of 0.13 or less. In some embodiments, the lipid nanoparticles have a polydispersity index (PDI) of 0.12 or less. In some embodiments, the lipid nanoparticles have a polydispersity index (PDI) of 0.11 or less. In some embodiments, the lipid nanoparticles have a polydispersity index (PDI) of 0.10 or less. In some embodiments, the lipid nanoparticles have a polydispersity index (PDI) of 0.09 or less. In some embodiments, the lipid nanoparticles have a polydispersity index (PDI) of 0.08 or less. In some embodiments, the lipid nanoparticles have a polydispersity index (PDI) of 0.07 or less. In some embodiments, the lipid nanoparticles have a polydispersity index (PDI) of 0.06 or less. In some embodiments, the lipid nanoparticles have a polydispersity index (PDI) of 0.05 or less.

In one aspect, the present invention provides, among other things, a method for delivery of messenger RNA (mRNA) for in vivo production of a protein or a peptide, comprising administering to a subject a stable composition according to the present invention.

In one aspect, the present invention provides, among other things, a method for delivery of messenger RNA (mRNA) for in vivo production of a protein or a peptide, comprising administering to a subject a stable composition according to the present invention, wherein the administering the stable composition does not results in anti-PEG antibodies and/or accelerated blood clearance (ABC) in the subject.

In one aspect, the present invention provides, among other things, a method of treating a subject having a deficiency in a protein or peptide, comprising administering to a subject in need of treatment a stable composition according the present invention.

In some embodiments, the administering the stable composition generates low to no anti-PEG antibodies in the subject.

In some embodiments, the administering the stable composition reduces or avoids accelerated blood clearance (ABC) in the subject.

In some embodiments, the stable composition is administered by intravenous injection.

In some embodiments, the stable composition is administered by pulmonary delivery.

In some embodiments, the stable composition is administered by intramuscular delivery.

In some embodiments, the administering of the stable composition results in expression of the protein or the peptide encoded by the mRNA for at least about 6 hours after administration. In some embodiments, the administering of the stable composition results in expression of the protein or the peptide encoded by the mRNA for at least about 12 hours after administration. In some embodiments, the administering of the stable composition results in expression of the protein or the peptide encoded by the mRNA for at least about 18 hours after administration. In some embodiments, the administering of the stable composition results in expression of the protein or the peptide encoded by the mRNA for at least about 24 hours after administration. In some embodiments, the administering of the stable composition results in expression of the protein or the peptide encoded by the mRNA for at least about 30 hours after administration. In some embodiments, the administering of the stable composition results in expression of the protein or the peptide encoded by the mRNA for at least about 36 hours after administration. In some embodiments, the administering of the stable composition results in expression of the protein or the peptide encoded by the mRNA for at least about 48 hours after administration. In some embodiments, the administering of the stable composition results in expression of the protein or the peptide encoded by the mRNA for at least about 72 hours after administration. In some embodiments, the administering of the stable composition results in expression of the protein or the peptide encoded by the mRNA for at least about 5 days after administration. In some embodiments, the administering of the stable composition results in expression of the protein or the peptide encoded by the mRNA for at least about 1 week after administration. In some embodiments, the administering of the stable composition results in expression of the protein or the peptide encoded by the mRNA for at least about 2 weeks after administration. In some embodiments, the administering of the stable composition results in expression of the protein or the peptide encoded by the mRNA for at least about 3 weeks after administration. In some embodiments, the administering of the stable composition results in expression of the protein or the peptide encoded by the mRNA for at least about 4 weeks after administration.

In one aspect, the present invention provides, among other things, a process of encapsulating messenger RNA (mRNA) in lipid nanoparticles comprising a step of mixing an mRNA solution and a lipid solution in the presence of a poloxamer.

In some embodiments, the lipid solution comprises one or more cationic lipids, one or more non-cationic lipids and less than 0.5% of PEG-modified lipids or PEG.

In some embodiments, the lipid solution comprises pre-formed lipid nanoparticles.

In some embodiments, wherein the mRNA solution and/or the lipid solution are at a pre-determined temperature higher than ambient temperature.

In some embodiments, the poloxamer is first added to the mRNA solution.

In some embodiments, the poloxamer is present in an amount lower than its critical micelle concentration (CMC).

In some embodiments, the poloxamer is present in an amount about 1% lower than its CMC. In some embodiments, the poloxamer is present in an amount about 2% lower than its CMC. In some embodiments, the poloxamer is present in an amount about 3% lower than its CMC. In some embodiments, the poloxamer is present in an amount about 4% lower than its CMC. In some embodiments, the poloxamer is present in an amount about 5% lower than its CMC. In some embodiments, the poloxamer is present in an amount about 6% lower than its CMC. In some embodiments, the poloxamer is present in an amount about 7% lower than its CMC. In some embodiments, the poloxamer is present in an amount about 8% lower than its CMC. In some embodiments, the poloxamer is present in an amount about 9% lower than its CMC. In some embodiments, the poloxamer is present in an amount about 10% lower than its CMC. In some embodiments, the poloxamer is present in an amount about 15% lower than its CMC. In some embodiments, the poloxamer is present in an amount about 20% lower than its CMC. In some embodiments, the poloxamer is present in an amount about 25% lower than its CMC. In some embodiments, the poloxamer is present in an amount about 30% lower than its CMC. In some embodiments, the poloxamer is present in an amount about 35% lower than its CMC. In some embodiments, the poloxamer is present in an amount about 40% lower than its CMC. In some embodiments, the poloxamer is present in an amount about 45% lower than its CMC. In some embodiments, the poloxamer is present in an amount about 50% lower than its CMC.

In some embodiments, the process further comprises a step of removing the poloxamer.

In some embodiments, the poloxamer is removed by dialysis.

In some embodiments, less than about 0.1% poloxamer remains upon removal. In some embodiments, less than about 0.05% poloxamer remains upon removal. In some embodiments, less than about 0.01% poloxamer remains upon removal.

In some embodiments, a residual amount of poloxamer remains upon removal.

In some embodiments, the amount of poloxamer remaining after removal is undetectable.

In some embodiments, the process does not include mixing any cholesterol lipids.

In one aspect, the present invention provides, among other things, a composition comprising lipid nanoparticles encapsulating mRNA formed according to a process disclosed herein.

In this application, the use of "or" means "and/or" unless stated otherwise. As used in this disclosure, the term "comprise" and variations of the term, such as "comprising" and "comprises," are not intended to exclude other additives, components, integers or steps. As used in this application, the terms "about" and "approximately" are used as equivalents. Both terms are meant to cover any normal fluctuations appreciated by one of ordinary skill in the relevant art.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The following figures are for illustration purposes only and not for limitation.

FIG. 6A depicts a chemistry reaction between the poloxamer and cobalt thiocyanate to form a blue precipitate. FIG. 6B shows a standard curve with known concentrations of poloxamer, measured at 624 nm.

DEFINITIONS

Figure 1:
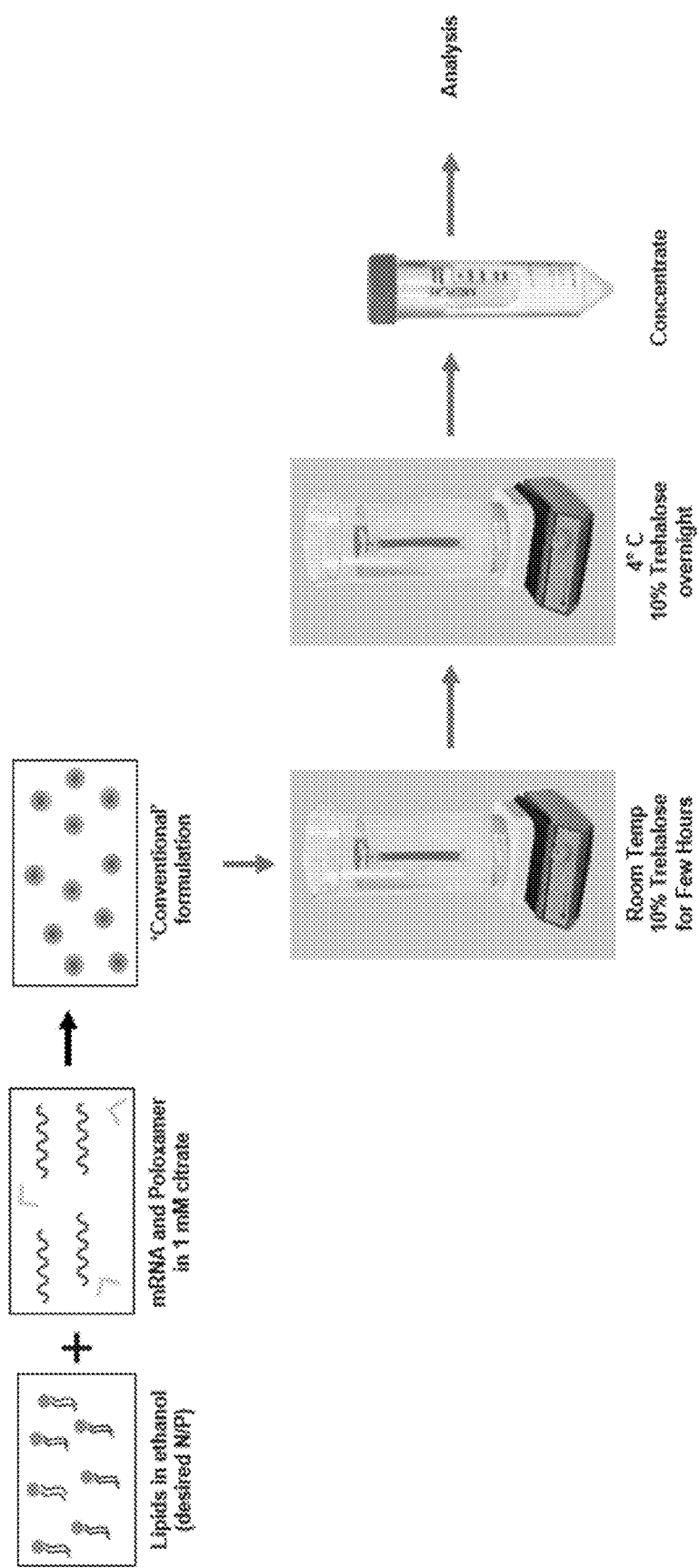
FIG. 1 shows a schematic of an exemplary LNP-mRNA encapsulation process that involves mixing an aqueous solution comprising mRNA and poloxamer with a lipid solution using a pump system to generate mRNA-LNPs in a LNP formation solution and then exchanging the LNP formation solution for a drug product formulation solution.

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Delivery: As used herein, the term "delivery" encompasses both local and systemic delivery. For example, delivery of mRNA encompasses situations in which an mRNA is delivered to a target tissue and the encoded protein or peptide is expressed and retained within the target tissue (also referred to as "local distribution" or "local delivery"), and situations in which an mRNA is delivered to a target tissue and the encoded protein or peptide is expressed and secreted into patient's circulation system (e.g., serum) and systematically distributed and taken up by other tissues (also referred to as "systemic distribution" or "systemic delivery").

Efficacy: As used herein, the term "efficacy," or grammatical equivalents, refers to an improvement of a biologically relevant endpoint, as related to delivery of mRNA that encodes a relevant protein or peptide. In some embodiments, the biological endpoint is protecting against an ammonium chloride challenge at certain timepoints after administration.

Encapsulation: As used herein, the term "encapsulation," or grammatical equivalent, refers to the process of confining an individual mRNA molecule within a nanoparticle.

Expression: As used herein, "expression" of a mRNA refers to translation of an mRNA into a peptide (e.g., an antigen), polypeptide, or protein (e.g., an enzyme) and also can include, as indicated by context, the post-translational modification of the peptide, polypeptide or fully assembled protein (e.g., enzyme). In this application, the terms "expression" and "production," and grammatical equivalent, are used inter-changeably.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control sample or subject (or multiple control samples or subjects) in the absence of the treatment described herein. A "control sample" is a sample subjected to the same conditions as a test sample, except for the test article. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

messenger RNA (mRNA): As used herein, the term "messenger RNA (mRNA)" refers to a polynucleotide that encodes at least one peptide, polypeptide or protein. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, O(6)-methylguanine, 2-thiocytidine, pseudouridine, and 5-methylcytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

N/P Ratio: As used herein, the term "N/P ratio" refers to a molar ratio of positively charged molecular units in the cationic lipids in a lipid nanoparticle relative to negatively charged molecular units in the mRNA encapsulated within that lipid nanoparticle. As such, N/P ratio is typically calculated as the ratio of moles of amine groups in cationic lipids in a lipid nanoparticle relative to moles of phosphate groups in mRNA encapsulated within that lipid nanoparticle.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, further improved compositions and processes for preparing mRNA-loaded lipid nanoparticles (mRNA-LNPs). Prior to the present invention, PEG-modified lipids typically were included in lipid nanoparticle (LNP) formulations as they were known to increase shelf stability and in vivo circulating time. On the other hand, PEG-modified lipids may induce accelerated blood clearance (ABC) and/or innate immune response by, among other things, producing anti-PEG antibodies. To address this issue, attempts have been made to prepare mRNA-LNPs without PEG-modified lipids. However, it has been observed that mRNA-loaded LNPs formed in the absence of PEG-modified lipids or PEG have large and unstable sizes, particularly after freeze and thaw, or tend to precipitate, rendering them unsuitable for therapeutic use. The present invention is, in part, based on the surprising discovery that unexpectedly stable mRNA-loaded LNPs with low or no PEG-modified lipids can be made by mixing the mRNA and lipids in the presence of amphiphilic block copolymer such as poloxamer. Thus, the present invention provides further improved mRNA-LNPs with exceptional stability and is particularly useful in cases where LNPs comprising low or no PEG-modified lipids are desired, for example, to avoid generating anti-PEG antibodies, and/or ABC.

The present invention provides inventive processes to encapsulate mRNA in LNPs and resulting stable mRNA-LNP compositions. In particular, the present invention provides a process of encapsulate mRNA in LNPs by mixing an mRNA solution and a lipid solution in the presence of an amphiphilic polymer (e.g., a poloxamer). The amphiphilic polymer may be removed from the mRNA-LNPs by, e.g., dialysis. The present invention is particularly useful in encapsulating mRNA in LNPs with low or no PEG-modified lipids.

Various aspects of the invention are described in detail in the following sections. The use of sections is not meant to limit the invention. Each section can apply to any aspect of the invention.

Processes of Encapsulating mRNA in LNPs

The present invention provides a process of encapsulating mRNA in LNPs in the presence of an amphiphilic polymer (e.g., a poloxamer). In some embodiments, a process of encapsulating mRNA described herein comprises a step of mixing a lipid solution with an mRNA solution in the presence of an amphiphilic polymer (e.g., a poloxamer) such that lipid nanoparticles encapsulating the mRNA are formed. In some embodiments, the amphiphilic polymer (e.g., a poloxamer) is present in the mRNA solution before mixing. In some embodiments, the amphiphilic polymer (e.g., a poloxamer) is present in the lipid solution before mixing. In some embodiments, the amphiphilic polymer (e.g., a poloxamer) is added during the mixing of an mRNA solution and a lipid solution.

In some embodiments, a suitable mRNA solution is an aqueous solution comprising mRNA encoding a protein or peptide of interest at a desired concentration. Various methods may be used to prepare a suitable mRNA solution. Exemplary methods are described in US 2016/0038432, US 2018/0153822 and US 2018/0125989, which are incorporated herein by reference.

In some embodiments, a suitable lipid solution comprises cationic lipids and non-cationic lipids (also referred to as helper lipids). In some embodiments, a suitable lipid solution comprises cationic lipids, non-cationic lipids (also referred to as helper lipids) and PEG-modified lipids or PEG. In some embodiments, a suitable lipid solution comprises cationic lipids, non-cationic lipids (also referred to as helper lipids), cholesterol-based lipids and PEG-modified lipids or PEG. Various lipids may be dissolved in a suitable solvent at desired respective amounts and/or ratios to prepare a lipid solution to be used in a process described herein. Various methods may be used to prepare a suitable lipid solution. Exemplary methods are described in US 2016/0038432, US 2018/0153822 and US 2018/0125989, which are incorporated herein by reference.

In some embodiments, a suitable lipid solution contains less than 1%, less than 0.9%, less than 0.8%, less than 0.7%, less than 0.6%, less than 0.5%, less than 0.4%, less than 0.3%, less than 0.2% or less than 0.1% of PEG-modified lipids or PEG of the total lipids by molar. In some embodiments, a suitable lipid solution contains less than 1%, less than 0.9%, less than 0.8%, less than 0.7%, less than 0.6%, less than 0.5%, less than 0.4%, less than 0.3%, less than 0.2% or less than 0.1% of PEG-modified lipids or PEG of the total lipids by weight. In some embodiments, a suitable lipid solution contains less than 0.09%, less than 0.08%, less than 0.07%, less than 0.06%, less than 0.05%, less than 0.04%, less than 0.03%, less than 0.02%, or less than 0.01% of PEG-modified lipids or PEG of the total lipids by molar. In some embodiments, a suitable lipid solution contains less than 0.09%, less than 0.08%, less than 0.07%, less than 0.06%, less than 0.05%, less than 0.04%, less than 0.03%, less than 0.02%, or less than 0.01% of PEG-modified lipids or PEG of the total lipids by weight.

Typically, an amphiphilic polymer (e.g., a poloxamer) is present in the mixture at an amount lower than its critical micelle concentration (CMC). In some embodiments, an amphiphilic polymer (e.g., a poloxamer) is present in the mixture at an amount about 1%, about 2%, about 3%, about 4%, about 5%, about 6%, about 7%, about 8%, about 9%, about 10%, about 15%, about 20%, about 25%, about 30%, about 35%, about 40%, about 45%, or about 50% lower than its CMC. In some embodiments, an amphiphilic polymer (e.g., a poloxamer) is present in the mixture at an amount about 0.9%, 0.8%, 0.7%, 0.6%, 0.5%, 0.4%, 0.3%, 0.2%, 0.1% lower than its CMC. In some embodiments, an amphiphilic polymer (e.g., a poloxamer) is present in the mixture at an amount about 55%, 60%, 65%, 70%, 75%, 80%, 90%, or 95% lower than its CMC.

In some embodiments, the mRNA solution or the lipid solution, or both, may be heated to a pre-determined temperature above the ambient temperature prior to mixing. In some embodiments, the mRNA solution and the lipid solution are heated to the pre-determined temperature separately prior to the mixing. In some embodiments, the mRNA solution and the lipid solution are mixed at the ambient temperature but then heated to the pre-determined temperature after the mixing. In some embodiments, the lipid solution is heated to the pre-determined temperature and mixed with mRNA solution at ambient temperature. In some embodiments, the mRNA solution is heated to the pre-determined temperature and mixed with the lipid solution at ambient temperature.

In some embodiments, the mRNA solution is heated to the pre-determined temperature by adding an mRNA stock solution that is at ambient temperature to a heated buffer solution to achieve the desired pre-determined temperature.

In some embodiments, mRNA-LNPs are heated post-formation. As shown in the Examples, it was surprisingly found that inclusion of a heating step during the process (before, during or after formation) provides for particularly higher encapsulation of mRNA-LNPs as compared to an otherwise identical process without the heating step.

As used herein, the term "ambient temperature" refers to the temperature in a room, or the temperature which surrounds an object of interest without heating or cooling. In some embodiments, the ambient temperature at which one or more of the solutions is maintained is or is less than about 35° C., 30° C., 25° C., 20° C., or 16° C. In some embodiments, the ambient temperature at which one or more of the solutions is maintained ranges from about 15-35° C., about 15-30° C., about 15-25° C., about 15-20° C., about 20-35° C., about 25-35° C., about 30-35° C., about 20-30° C., about 25-30° C. or about 20-25° C. In some embodiments, the ambient temperature at which one or more of the solutions is maintained is 20-25° C.

Therefore, a pre-determined temperature greater than ambient temperature is typically greater than about 25° C. In some embodiments, a pre-determined temperature suitable for the present invention is or is greater than about 30° C., 37° C., 40° C., 45° C., 50° C., 55° C., 60° C., 65° C., or 70° C. In some embodiments, a pre-determined temperature suitable for the present invention ranges from about 25-70° C., about 30-70° C., about 35-70° C., about 40-70° C., about 45-70° C., about 50-70° C., or about 60-70° C. In particular embodiments, a pre-determined temperature suitable for the present invention is about 65° C.

In some embodiments, the mRNA solution and the lipid solution are mixed using a pump. As the encapsulation procedure with such mixing can occur on a wide range of scales, different types of pumps may be used to accommodate desired scale. It is however generally desired to use a pulse-less flow pump. As used herein, a pulse-less flow pump refers to any pump that can establish a continuous flow with a stable flow rate. Types of suitable pumps may include, but are not limited to, gear pumps and centrifugal pumps. Exemplary gear pumps include, but are not limited to, Cole-Parmer or Diener gear pumps. Exemplary centrifugal pumps include, but are not limited to, those manufactured by Grainger or Cole-Parmer.

The mRNA solution and the lipid solution may be mixed at various flow rates. Typically, the mRNA solution may be mixed at a rate greater than that of the lipid solution. For example, the mRNA solution may be mixed at a rate at least 1×, 2×, 3×, 4×, 5×, 6×, 7×, 8×, 9×, 10×, 15×, or 20× greater than the rate of the lipid solution.

Suitable flow rates for mixing may be determined based on the scales. In some embodiments, an mRNA solution is mixed at a flow rate ranging from about 40-400 ml/minute, 60-500 ml/minute, 70-600 ml/minute, 80-700 ml/minute, 90-800 ml/minute, 100-900 ml/minute, 110-1000 ml/minute, 120-1100 ml/minute, 130-1200 ml/minute, 140-1300 ml/minute, 150-1400 ml/minute, 160-1500 ml/minute, 170-1600 ml/minute, 180-1700 ml/minute, 150-250 ml/minute, 250-500 ml/minute, 500-1000 ml/minute, 1000-2000 ml/minute, 2000-3000 ml/minute, 3000-4000 ml/minute, or 4000-5000 ml/minute. In some embodiments, the mRNA solution is mixed at a flow rate of about 200 ml/minute, about 500 ml/minute, about 1000 ml/minute, about 2000 ml/minute, about 3000 ml/minute, about 4000 ml/minute, or about 5000 ml/minute.

In some embodiments, the lipid solution is mixed at a flow rate ranging from about 25-75 ml/minute, 20-50 ml/minute, 25-75 ml/minute, 30-90 ml/minute, 40-100 ml/minute, 50-110 ml/minute, 75-200 ml/minute, 200-350 ml/minute, 350-500 ml/minute, 500-650 ml/minute, 650-850 ml/minute, or 850-1000 ml/minute. In some embodiments, the lipid solution is mixed at a flow rate of about 50 ml/minute, about 100 ml/minute, about 150 ml/minute, about 200 ml/minute, about 250 ml/minute, about 300 ml/minute, about 350 ml/minute, about 400 ml/minute, about 450 ml/minute, about 500 ml/minute, about 550 ml/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 ml/minute.

Typically, an inventive process described herein includes a step of removing the amphiphilic polymer (e.g., the poloxamer). In some embodiments, the amphiphilic polymer (e.g., the poloxamer) added during the process is subsequently removed after the formation of mRNA-LNPs. For example, amphiphilic polymers (e.g., poloxamers) may be removed by buffer exchange techniques such as dialysis. In some embodiments, the LNP formation solution is exchanged into a solution that constitutes the product formulation solution. For example, the mixture containing the formed mRNA-LNPs may be dialyzed in one or more formulation solutions to remove the amphiphilic polymer (e.g., the poloxamer) present during the mRNA-LNP formation. Suitable formulations are known in the art and exemplary formulations are described in the Formulations section in this application.

The exchange of solution comprising mRNA-LNPs from LNP formation solution to formulation solutions can be achieved by any of a variety of buffer exchange techniques known in the art. In some embodiments, the step of exchanging the LNP formation solution for a formulation solution is accompanied by purification and/or concentration of mRNA-LNPs. Various methods may be used to achieve the exchange of solution together with purification of mRNA-LNPs or concentration of mRNA-LNPs in the solution.

For example, in some embodiments, this exchange of solution is achieved by diafiltration. Diafiltration is a fractionation process whereby small undesired particles are passed through a filter while larger desired nanoparticles are maintained in the retentate without changing the concentration of those nanoparticles in solution. Diafiltration is often used to remove salts or reaction buffers from a solution. Diafiltration may be either continuous or discontinuous. In continuous diafiltration, a diafiltration solution is added to the sample feed at the same rate that filtrate is generated. In discontinuous diafiltration, the solution is first diluted and then concentrated back to the starting concentration. Discontinuous diafiltration may be repeated until a desired concentration of nanoparticles is reached.

In some embodiments, the solution is exchanged and the mRNA-LNPs are purified using Tangential Flow Filtration. Tangential flow filtration (TFF), also referred to as cross-flow filtration, is a type of filtration wherein the material to be filtered is passed tangentially across a filter rather than through it. In TFF, undesired permeate passes through the filter, while the desired retentate (mRNA-LNPs and free mRNA) passes along the filter and is collected downstream. In some embodiments, the desired material is contained in the retentate in TFF, which is the opposite of what one normally encounters in traditional-dead end filtration.

Various TFF techniques are known and can be used to practice the present invention. Exemplary TFF purification methods are described in US 2016/0040154 and US 2015/0376220, which are incorporated herein by reference.

In some embodiments, the encapsulation of mRNA in the LNPs can be further enhanced by heating the formulation solution that comprises the mRNA-LNPs as well as some free mRNA that was not encapsulated in the LNP formation solution to a pre-determined temperature as described herein.

In some embodiments, less than about 0.1%, 0.09%, 0.08%, 0.07%, 0.06%, 0.05%, 0.04%, 0.03%, 0.02%, or 0.01% of the original amount of the amphiphilic polymer (e.g., the poloxamer) present in the mixture remains upon removal. In some embodiments, a residual amount of the amphiphilic polymer (e.g., the poloxamer) remains in a formulation upon removal. As used herein, a residual amount means a remaining amount after substantially all of the substance (an amphiphilic polymer described herein such as a poloxamer) in a composition is removed. A residual amount may be detectable using a known technique qualitatively or quantitatively. A residual amount may not be detectable using a known technique.

In some embodiments, excessive mRNA is also removed, together with the amphiphilic polymer (e.g., the poloxamer) present during formation of mRNA-LNPs.

Amphiphilic Block Copolymers

Various amphiphilic block copolymers may be used to practice the present invention. In some embodiments, an amphiphilic block copolymer is also referred to as a surfactant or a non-ionic surfactant.

In some embodiments, an amphiphilic polymer suitable for the invention is selected from poloxamers (Pluronic®), poloxamines (Tetronic®), polyoxyethylene glycol sorbitan alkyl esters (polysorbates) and polyvinyl pyrrolidones (PVPs).

Poloxamers

In some embodiments, a suitable amphiphilic polymer is a poloxamer. For example, a suitable poloxamer is of the following structure:

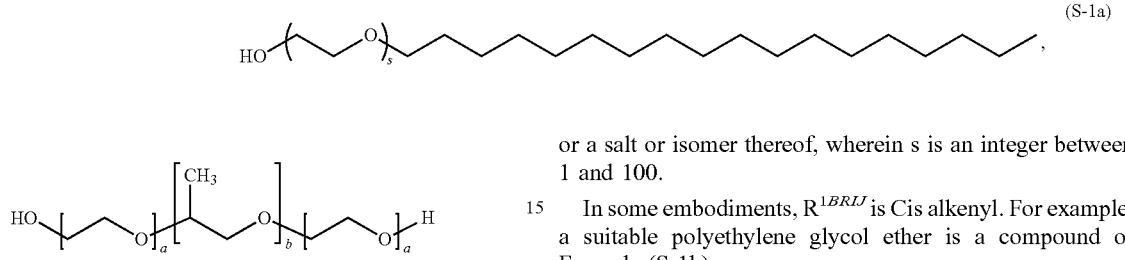

wherein a is an integer between 10 and 150 and b is an integer between 20 and 60. For example, a is about 12 and b is about 20, or a is about 80 and b is about 27, or a is about 64 and b is about 37, or a is about 141 and b is about 44, or a is about 101 and b is about 56.

In some embodiments, a poloxamer suitable for the invention has ethylene oxide units from about 10 to about 150. In some embodiments, a poloxamer has ethylene oxide units from about 10 to about 100.

Other Amphiphilic Polymers

In some embodiments, an amphiphilic polymer is a poloxamine, e.g., tetronic 304 or tetronic 904.

In some embodiments, an amphiphilic polymer is a polyvinylpyrrolidone (PVP), such as PVP with molecular weight of 3 kDa, 10 kDa, or 29 kDa.

In some embodiments, an amphiphilic polymer is a polyethylene glycol ether (Brij), polysorbate, sorbitan, and derivatives thereof. In some embodiments, an amphiphilic polymer is a polysorbate, such as PS 20.

In some embodiments, an amphiphilic polymer is a polyethylene glycol ether. In some embodiments, a suitable polyethylene glycol ether is a compound of Formula (S-1):

(S-1)

or a salt or isomer thereof, wherein t is an integer between 1 and 100; $R^{1BRIJ}$ independently is Cio-40 alkyl, Cio-40 alkenyl, or Cio-40 alkynyl; and optionally one or more methylene groups of $R^{5PEG}$ are independently replaced with C3-10 carbocyclylene, 4 to 10 membered heterocyclylene, C6-10 arylene, 4 to 10 membered heteroarylene, —N($R^N$)-, -O-, —S—, —C(O)—, —C(O)N($R^N$)—, —$NR^N$C(O)—, —NR C(O)N(R)—, —C(O)0-, —OC(O)—, —OC(O)0-OC(O)N($R^N$)—, —$NR^N$C(O)0-C(O)S——SC(O)—, —C(=$NR^N$)—, —C(=NR)N(R)—, —NRNC(=$NR^N$)— —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)0-OS(O)0-OS(O)$_2$— —S(O)$_2$0-OS(O)$_2$0-N($R^N$)S(O)—, —S(O)N($R^N$)— —N($R^N$)S(O)N($R^N$)— —OS(O)N($R^N$)— —N($R^N$)S(O)0-S(O)$_2$— —N($R^N$)S(O)$_2$— —S(O)$_2$N($R^N$)—, —N($R^N$)S(O)$_2$N($R^N$)— —OS(O)$_2$N($R^N$)— or —N($R^N$)S(O)$_2$0-; and each instance of $R^N$ is independently hydrogen, $C_{1-6}$ alkyl, or a nitrogen protecting group.

In some embodiment, $R^{1BRIJ}$ is Cis alkyl. For example, the polyethylene glycol ether is a compound of Formula (S-1a):

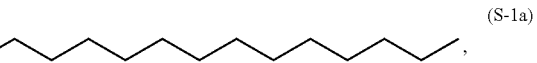

(S-1a)

or a salt or isomer thereof, wherein s is an integer between 1 and 100.

In some embodiments, $R^{1BRIJ}$ is Cis alkenyl. For example, a suitable polyethylene glycol ether is a compound of Formula (S-1b):

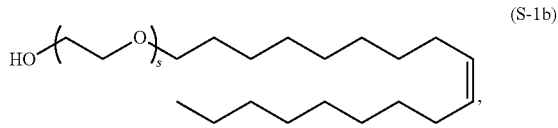

(S-1b)

or a salt or isomer thereof, wherein s is an integer between 1 and 100.

Stable mRNA-LNP Compositions

Among other things, the invention provides mRNA-LNPs prepared using an inventive process described herein. In particular, the invention provides stable compositions comprising mRNA-LNPs with low (e.g., <0.5% by weight or by molar) or no PEG-modified lipids or PEG. Such mRNA-LNPs are suitable for effective delivery and expression of mRNA in vivo. In this application, LNPs and mRNA-LNPs are used inter-changeably unless specifically indicated. For example, mRNA-LNPs used herein include both mRNA-loaded LNPs and empty LNPs unless specifically identified.

Typically, the term "stable" in connection of an LNP composition means an LNP composition that can be stored at room temperature for more than 2 hours or at 4° C. Celsius over night without precipitation.

In some embodiments, a stable composition described herein comprises LNPs that maintain an average diameter within 60% of the original average size following one or more freeze thaw cycles.

Cationic Lipids

As used herein, the term "cationic lipids" refers to any of a number of lipid and lipidoid species that have a net positive charge at a selected pH, such as at physiological pH. Several cationic lipids have been described in the literature, many of which are commercially available.

Suitable cationic lipids for use in the compositions and methods of the invention include the cationic lipids as described in International Patent Publication WO 2010/144740, which is incorporated herein by reference. In certain embodiments, the compositions and methods of the present invention include a cationic lipid, (6Z,9Z,28Z,31Z)-heptatriaconta-6,9,28,31-tetraen-19-yl 4-(dimethylamino) butanoate, having a compound structure of:

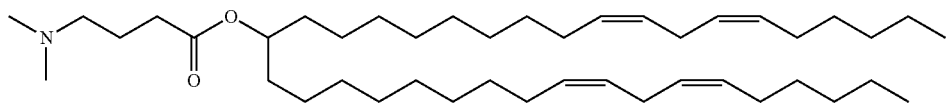 [SMILES: CCCCC/C=C\C/C=C\CCCCCCCCC(CCCCCCCC/C=C\C/C=C\CCCCC)OC(=O)CCCN(C)C]

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

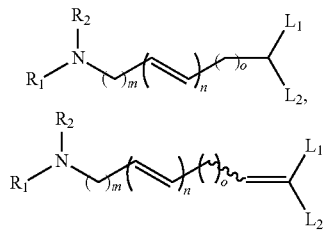

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z, 18Z)-N,N-dimethyl-6-(9Z,12Z)-octadeca-9,12-dien-1-yl) tetracosa-15,18-dien-1-amine ("HGT5000"), having a compound structure of:

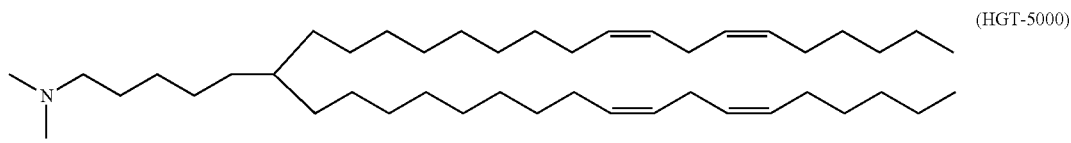 [SMILES: CCCCC/C=C\C/C=C\CCCCCCCCC(CCCCCCCC/C=C\C/C=C\CCCCC)CCCCCN(C)C]

(HGT-5000)

and pharmaceutically acceptable salts thereof. In certain embodiments, the compositions and methods of the present invention include the cationic lipid (15Z, 18Z)-N,N-dimethyl-6-((9Z,12Z)-octadeca-9,12-dien-1-yl) tetracosa-4,15,18-trien-1-amine ("HGT5001"), having a compound structure of:

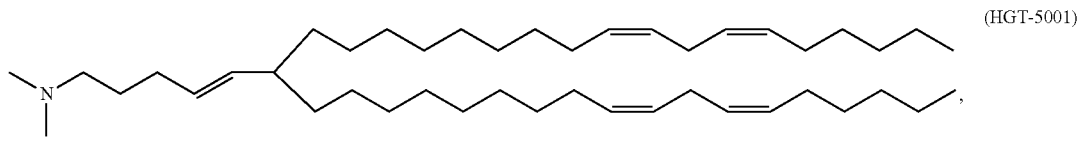 [SMILES: CCCCC/C=C\C/C=C\CCCCCCCCC(/C=C/CCCN(C)C)CCCCCCCC/C=C\C/C=C\CCCCC]

(HGT-5001)

and pharmaceutically acceptable salts thereof. In certain embodiments, the compositions and methods of the present invention include the cationic lipid and (15Z,18Z)-N,N-dimethyl-6-((9Z,12Z)-octadeca-9,12-dien-1-yl) tetracosa-5,15,18-trien-1-amine ("HGT5002"), having a compound structure of:

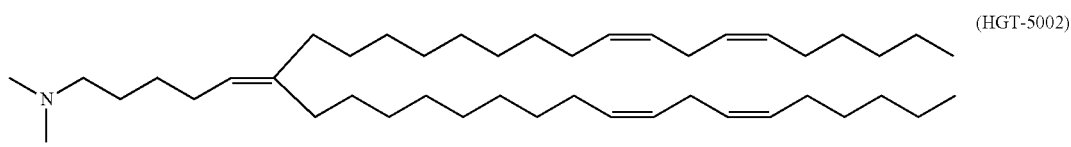 [SMILES: CCCCC/C=C\C/C=C\CCCCCCCCC(=CCCCCN(C)C)CCCCCCCC/C=C\C/C=C\CCCCC]

(HGT-5002)

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

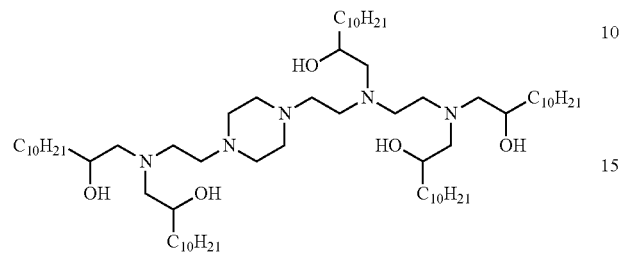

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

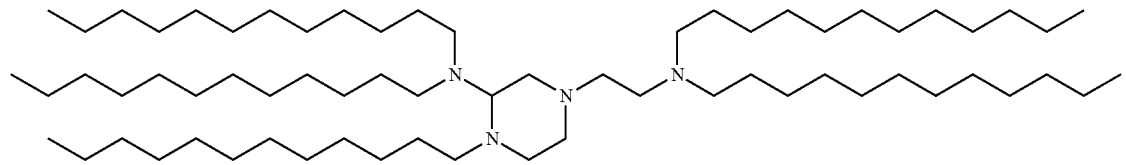 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

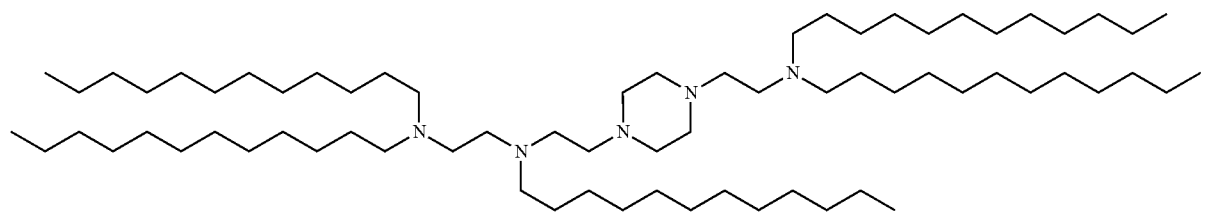 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

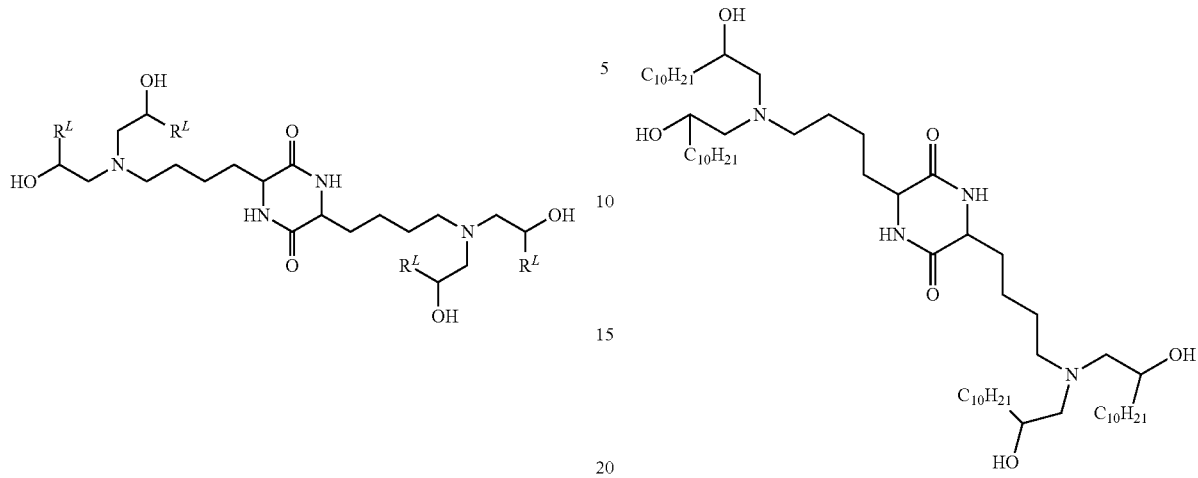

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

(cKK-E12)

and pharmaceutically acceptable salts thereof. In certain embodiments, the compositions and methods of the present invention include a cationic lipid having a compound structure of:

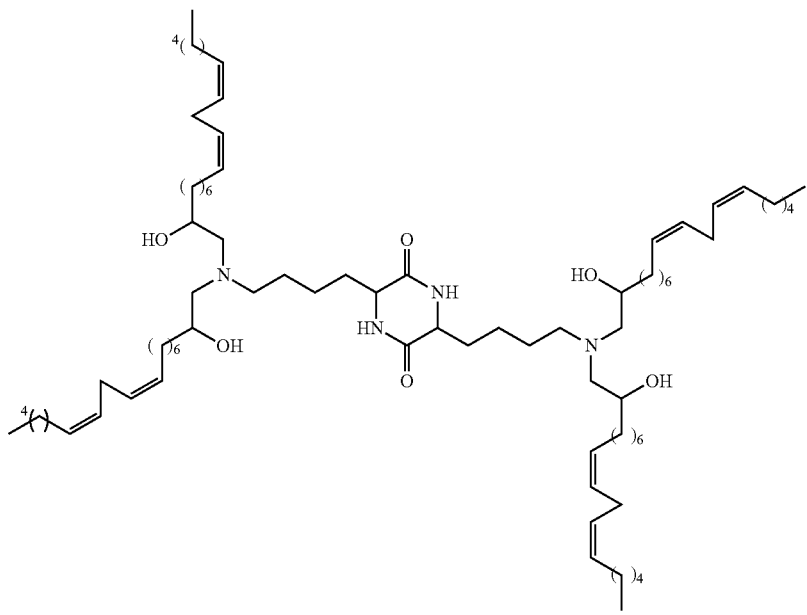

(OF-02)

and pharmaceutically acceptable salts thereof. In certain embodiments, the compositions and methods of the present invention include a cationic lipid having a compound structure of:

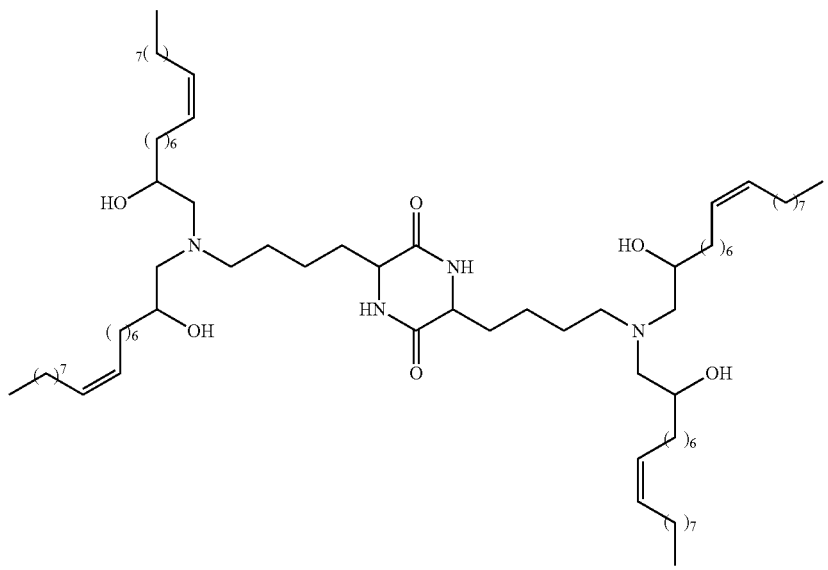

and pharmaceutically acceptable salts thereof. In certain embodiments, the compositions and methods of the present invention include a cationic lipid having a compound structure of:

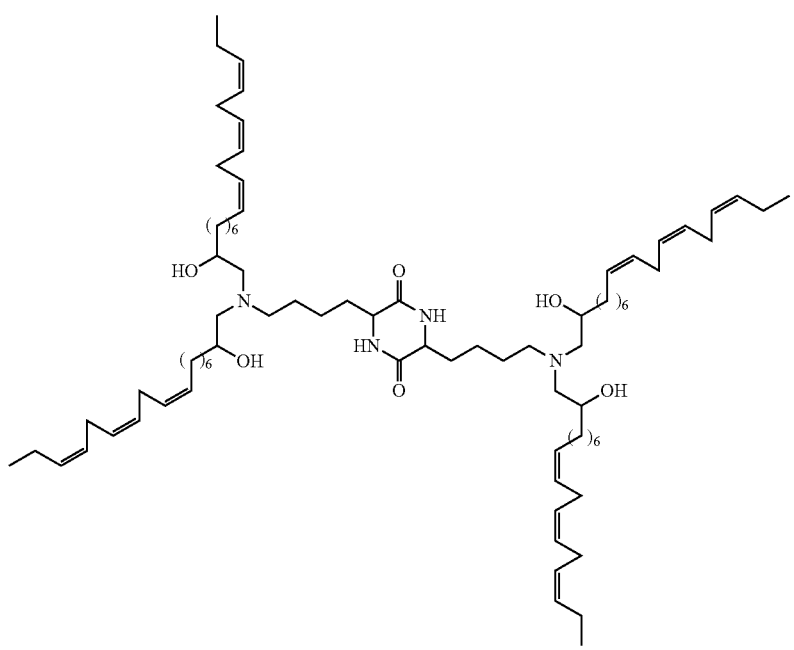

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

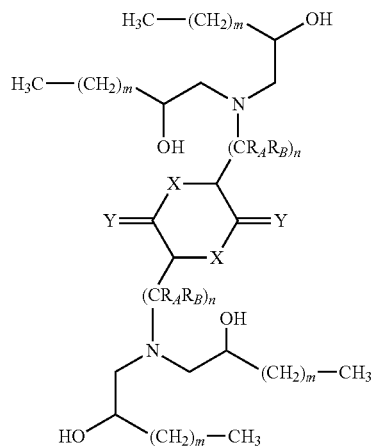

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each $R_B$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

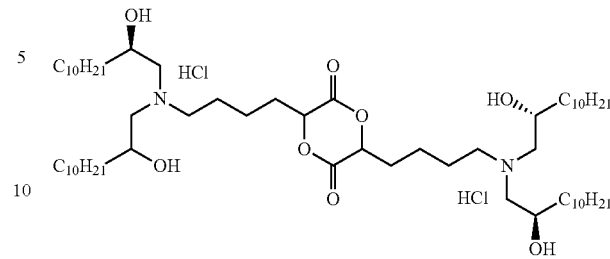

(Target 23)

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

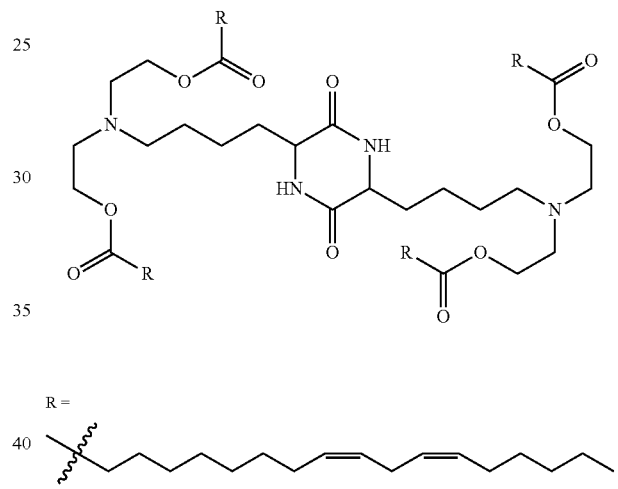

or a pharmaceutically acceptable salt thereof. In some embodiments, the compositions and methods of the present invention include a cationic lipid having the compound structure:

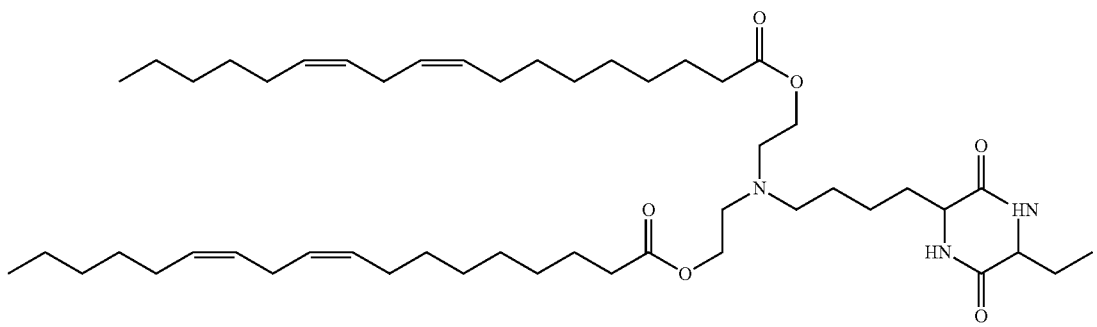 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

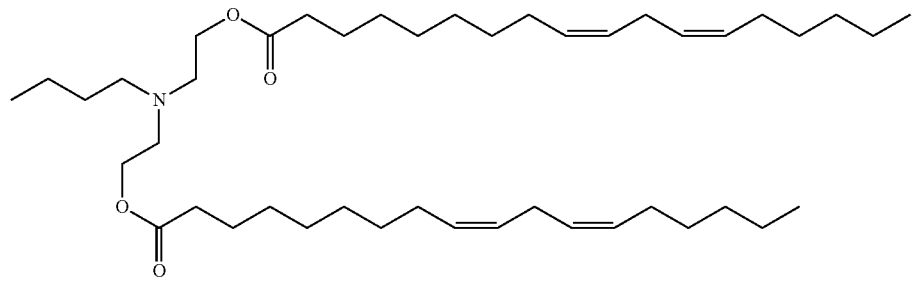 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

Other suitable cationic lipids for use in the compositions and methods of the present invention include cationic lipids as described in U.S. Provisional Patent Application Ser. No. 62/758,179, which is incorporated herein by reference. In some embodiments, the compositions and methods of the present invention include a cationic lipid of the following formula:

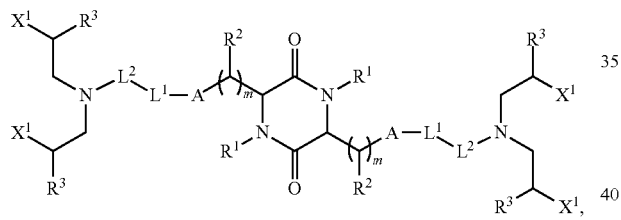

or a pharmaceutically acceptable salt thereof, wherein each $R^1$ and $R^2$ is independently H or $C_1$-$C_6$ aliphatic; each m is independently an integer having a value of 1 to 4; each A is independently a covalent bond or arylene; each $L^1$ is independently an ester, thioester, disulfide, or anhydride group; each $L^2$ is independently $C_2$-$C_{10}$ aliphatic; each $X^1$ is independently H or OH; and each $R^3$ is independently $C_6$-$C_{20}$ aliphatic. In some embodiments, the compositions and methods of the present invention include a cationic lipid of the following formula:

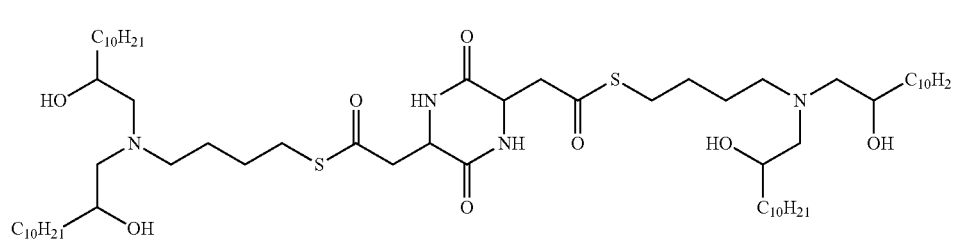

(Compound 1)

or a pharmaceutically acceptable salt thereof. In some embodiments, the compositions and methods of the present invention include a cationic lipid of the following formula:

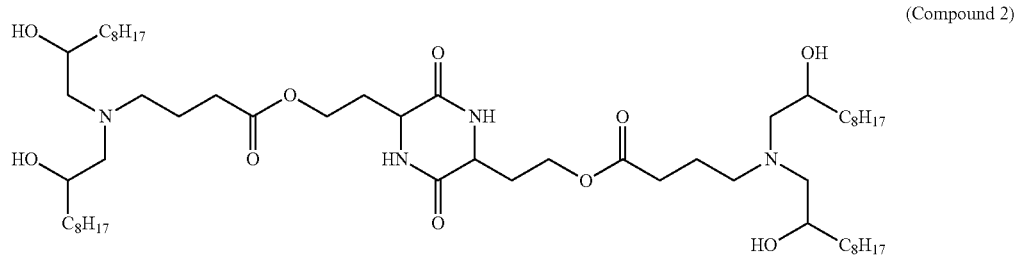

(Compound 2)

or a pharmaceutically acceptable salt thereof. In some embodiments, the compositions and methods of the present invention include a cationic lipid of the following formula:

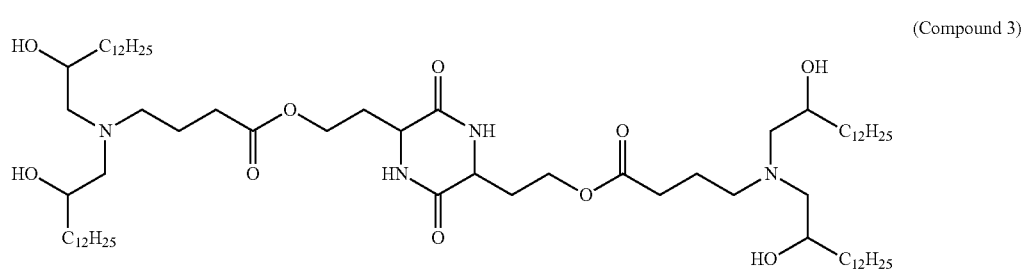

(Compound 3)

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

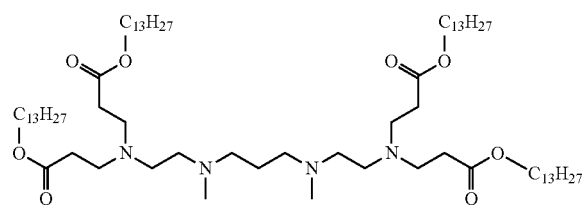

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

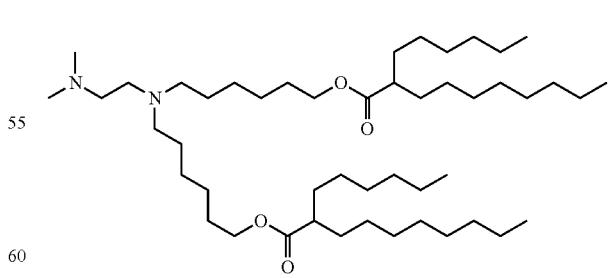

and pharmaceutically acceptable salts thereof. In some embodiments, the compositions and methods of the present invention include a cationic lipid having the compound structure:

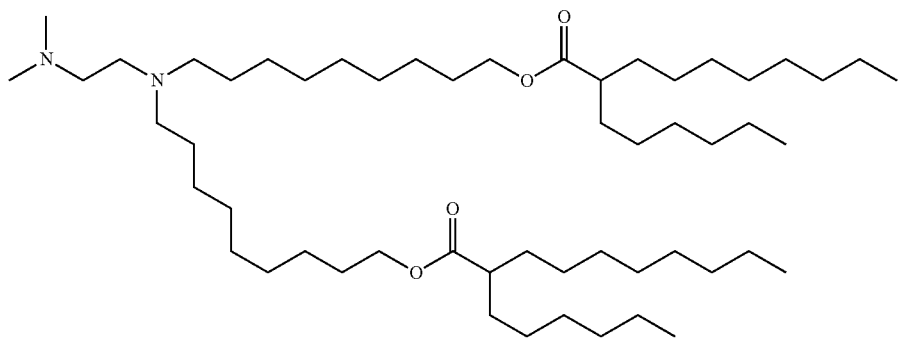 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

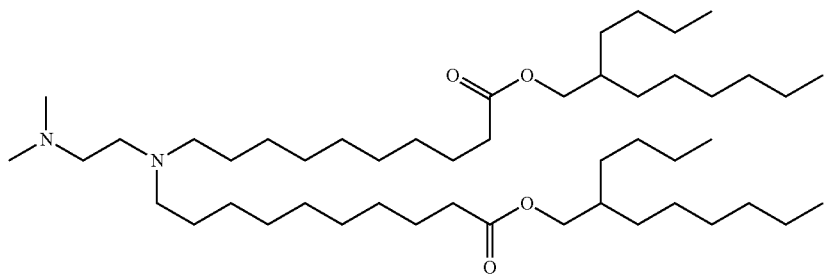 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound structure:

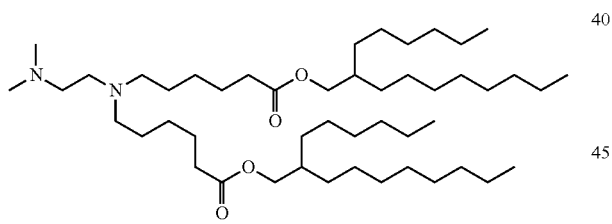

and pharmaceutically acceptable salts thereof. In some embodiments, the compositions and methods of the present invention include a cationic lipid having the compound structure:

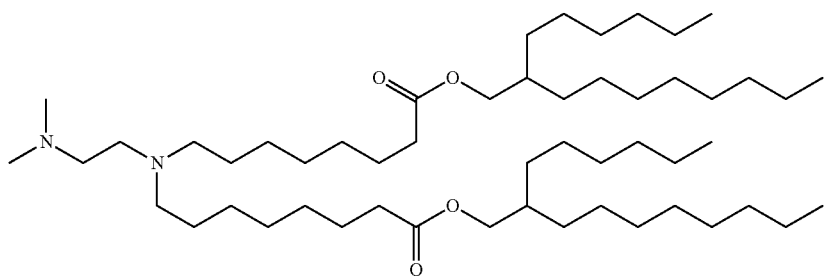 [SMILES: CCCCCCCCC(CCCCCC)COC(=O)CCCCCCCN(CCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

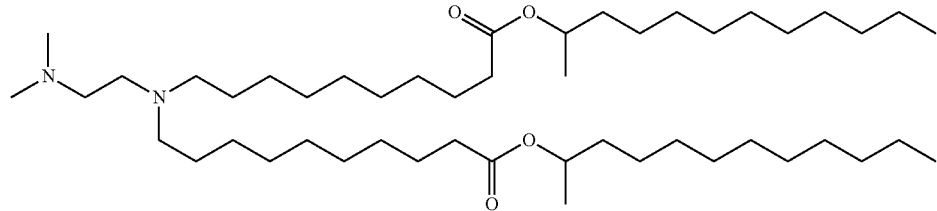 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

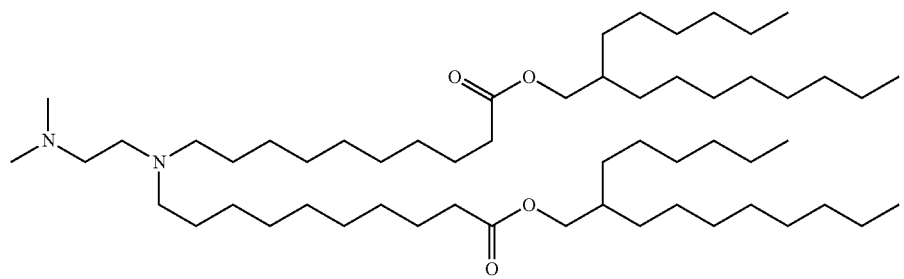 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

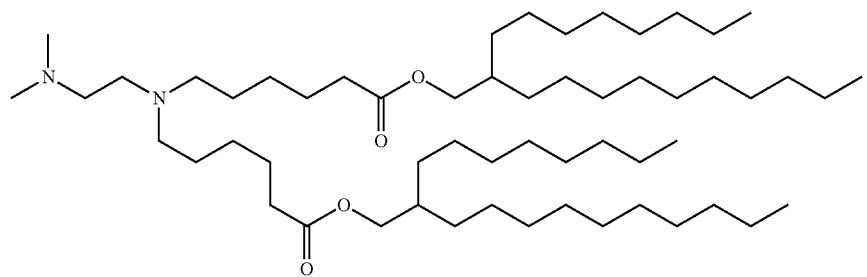 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

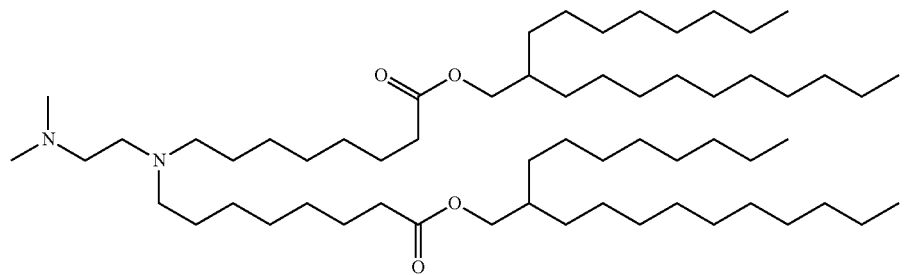 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

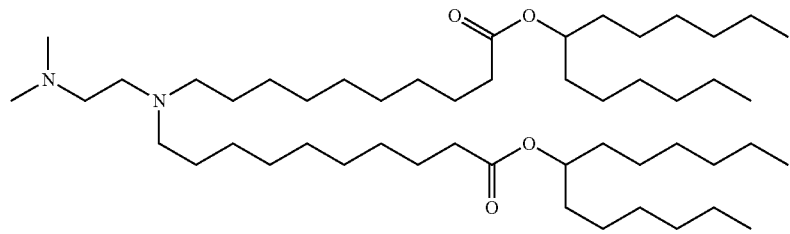 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

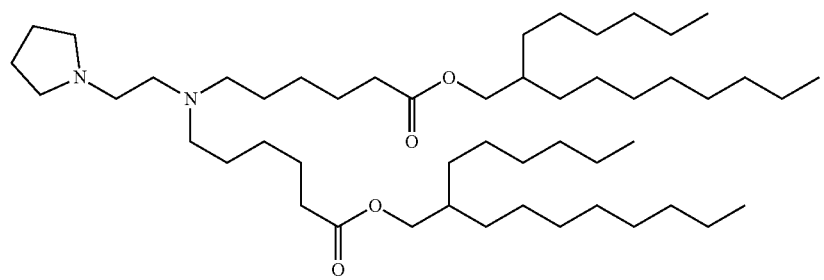 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

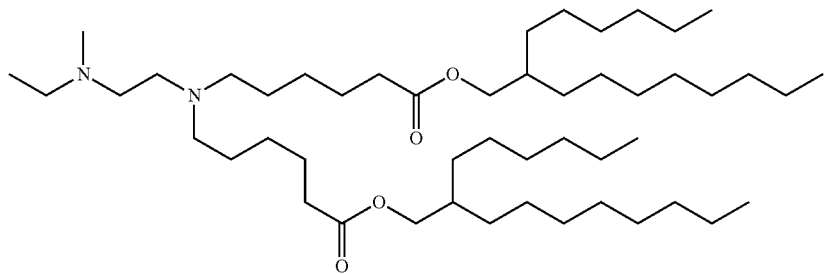 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

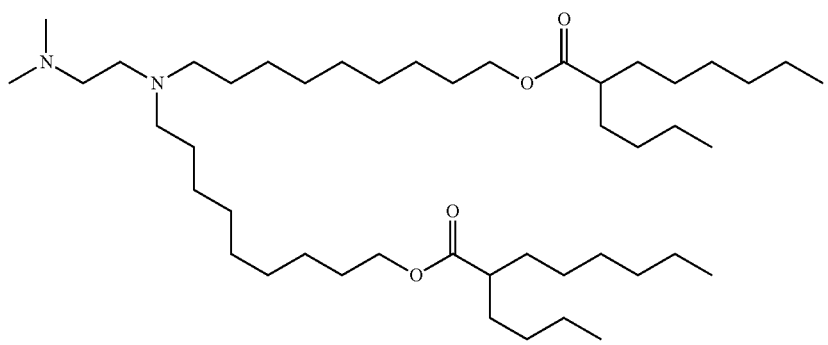 [SMILES: CCCCCCC(CCCC)C(=O)OCCCCCCCCCN(CCCCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

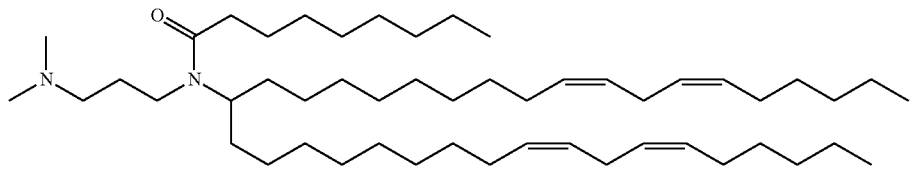 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

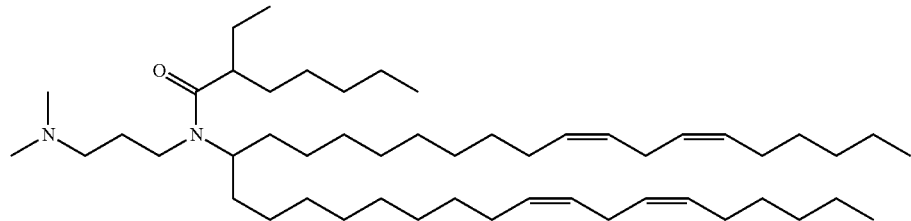 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

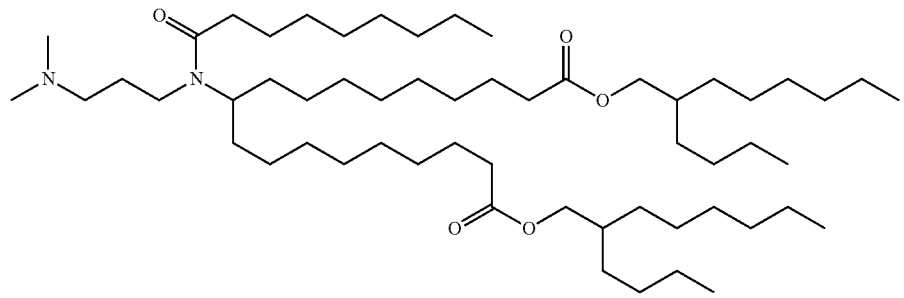 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

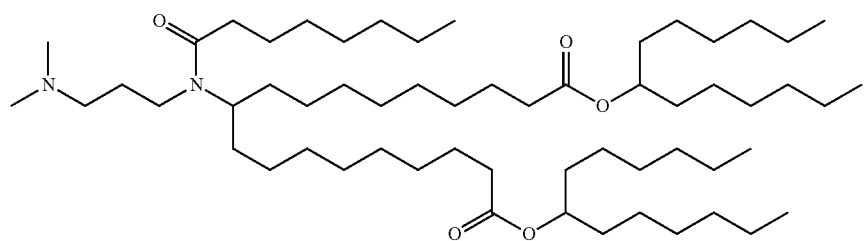 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

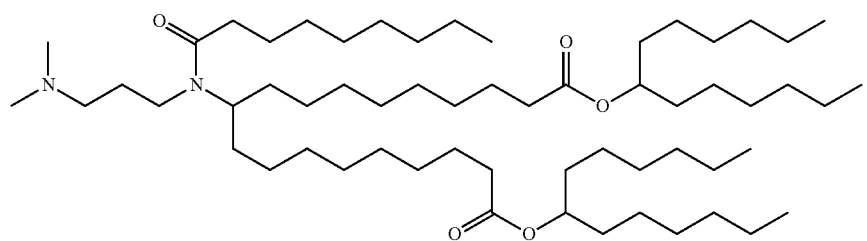 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

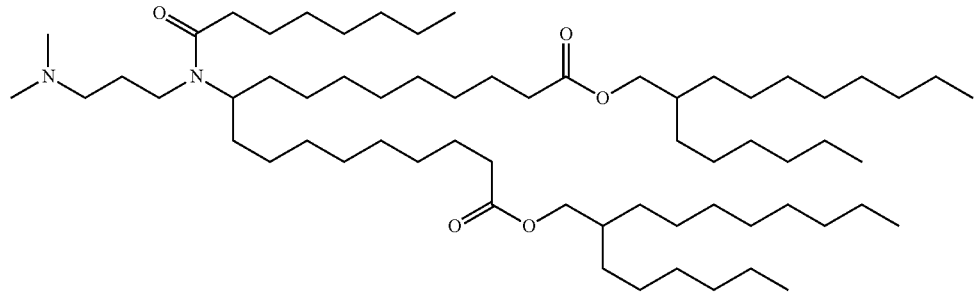 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

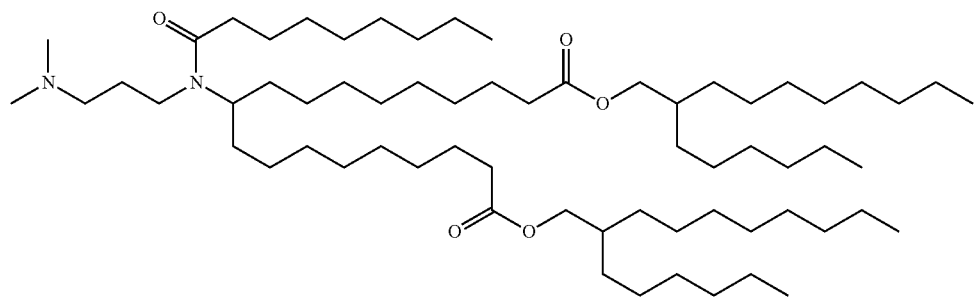 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

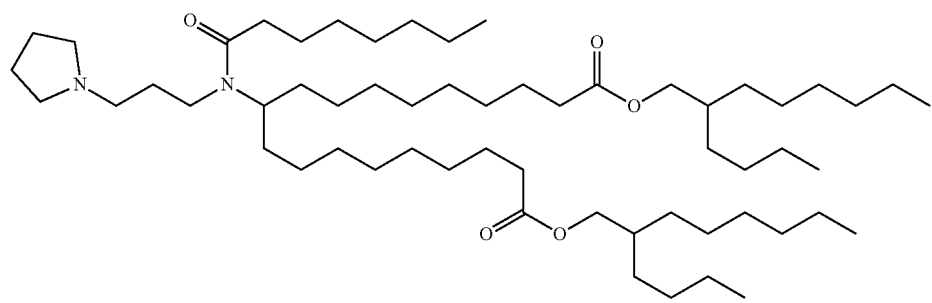 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

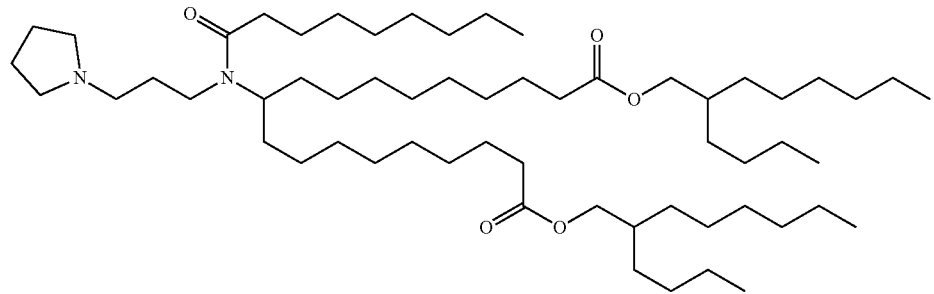 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

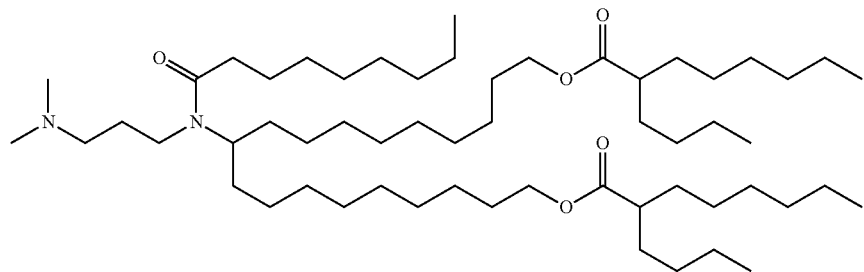 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

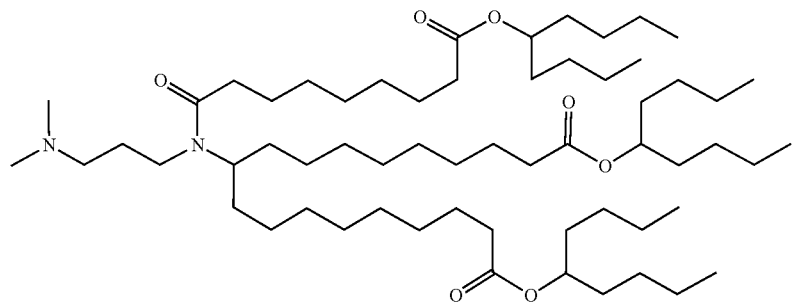 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

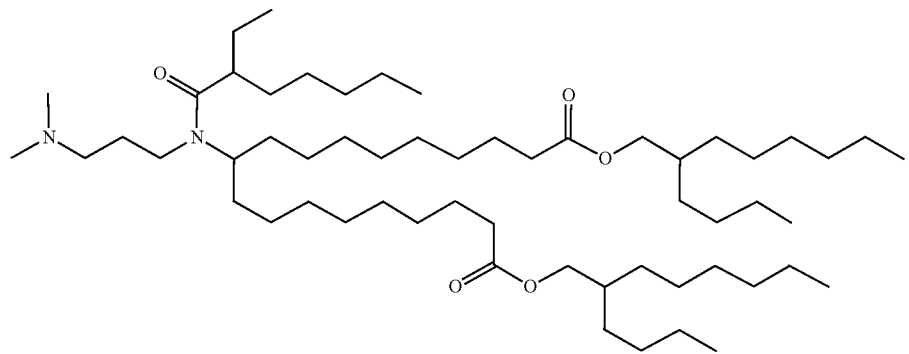 [SMILES: CCCCCCC(CCCC)COC(=O)CCCCCCCCC(CCCCCCCCC(=O)OCC(CCCC)CCCCC(C)C)N(CCCN(C)C)C(=O)C(CC)CCCCC]

and pharmaceutically acceptable salts thereof. In some embodiments, the compositions and methods of the present invention include a cationic lipid having the compound structure:

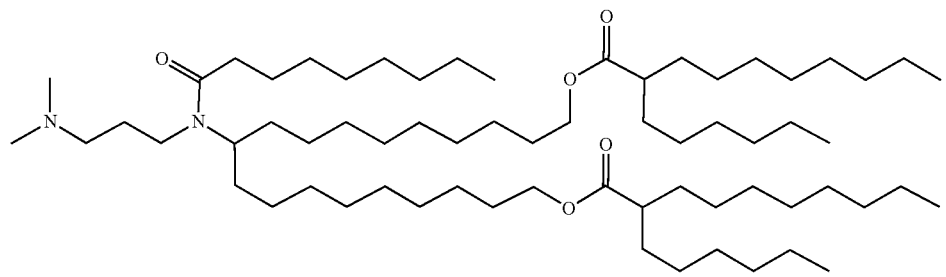 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

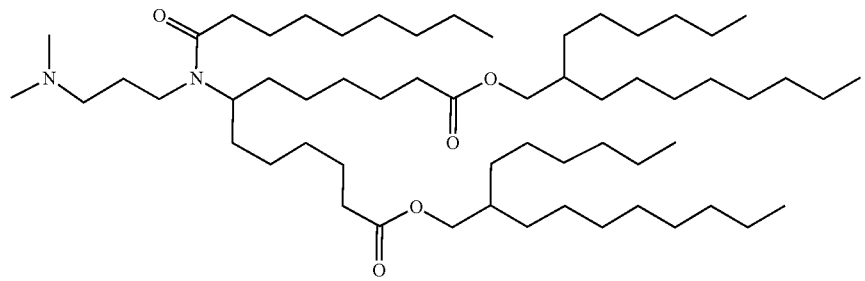

and pharmaceutically acceptable salts thereof. In some embodiments, the compositions and methods of the present invention include a cationic lipid having the compound structure:

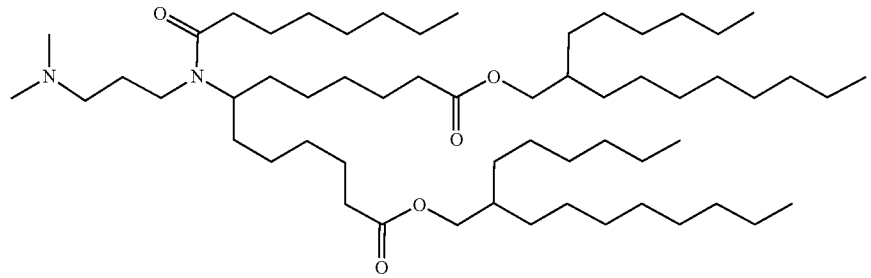 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

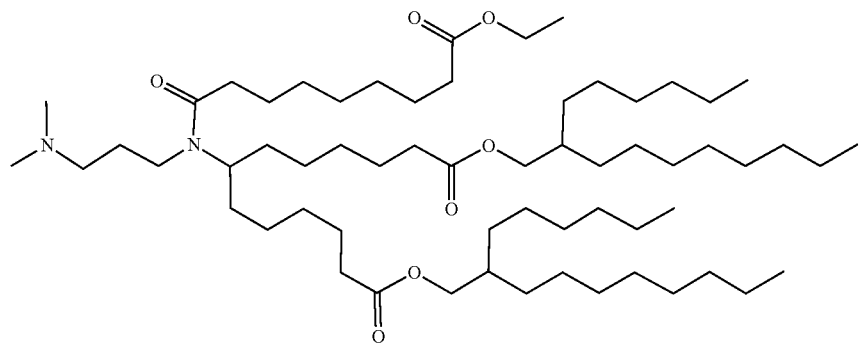 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

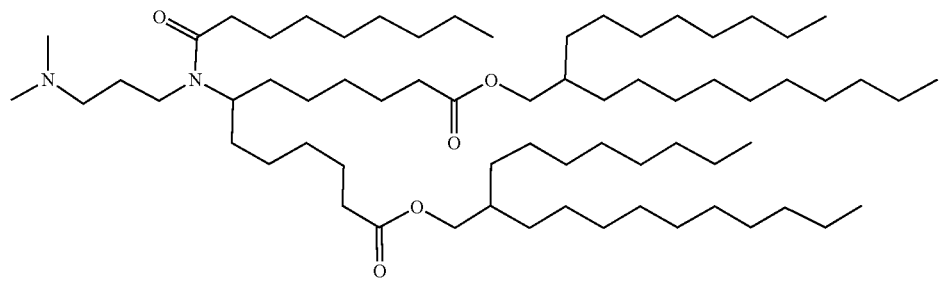 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

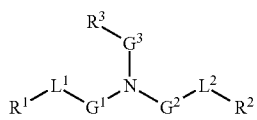

or a pharmaceutically acceptable salt thereof, wherein one of $L^1$ or $L^2$ is —O(C=O)—, —(C=O)O—, —C(=O)—, —O—, —S(O)$_x$, —S—S—, —C(=O)S—, —SC(=O)—, —NR$^a$C(=O)—, —C(=O)NR$^a$—, NR$^a$C(=O)NR$^a$—, —OC(=O)NR$^a$—, or —NR$^a$C(=O)O—; and the other of $L^1$ or $L^2$ is —O(C=O)—, —(C=O)O—, —C(=O)—, —O—, —S(O)$_x$, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl; $R^1$ and $R^2$ are each independently $C_6$-$C_{24}$ alkyl or $C_6$-$C_{24}$ alkenyl; $R^3$ is H, OR$^5$, CN, —C(=O)OR$^4$, —OC(=O)R$^4$ or —NR$^4$C(=O)R$^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

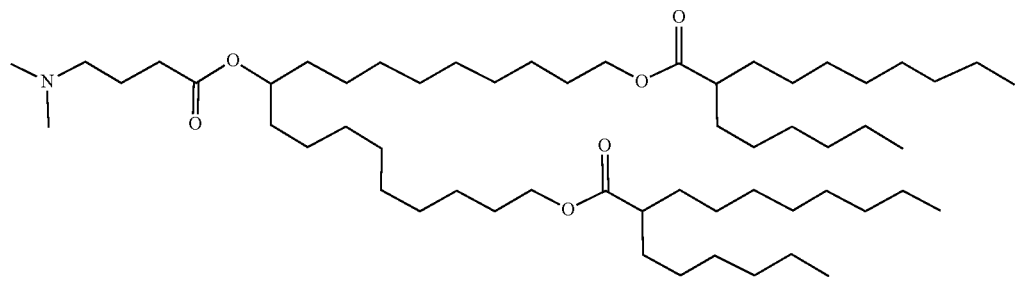 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

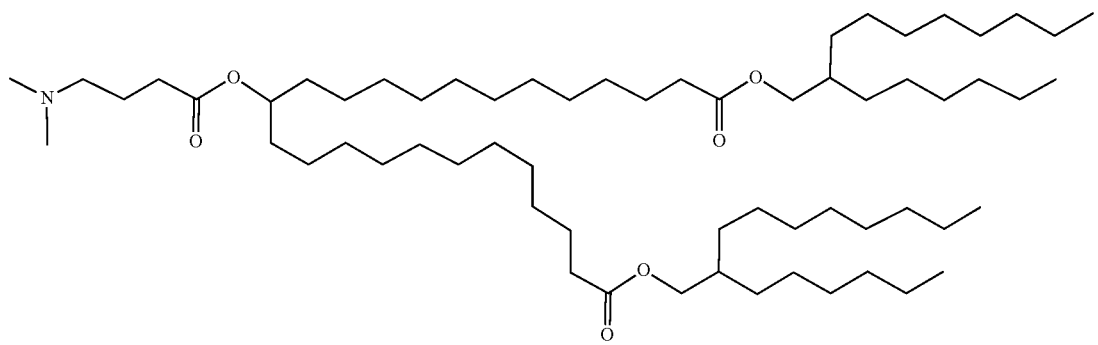 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

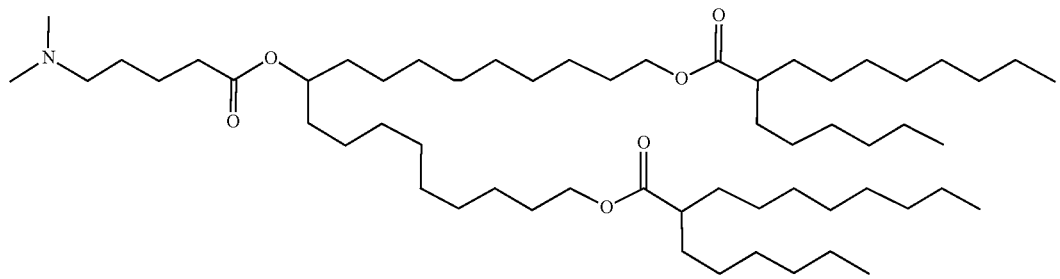 [SMILES: CCCCCCCCC(CCCCCC)C(=O)OCCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

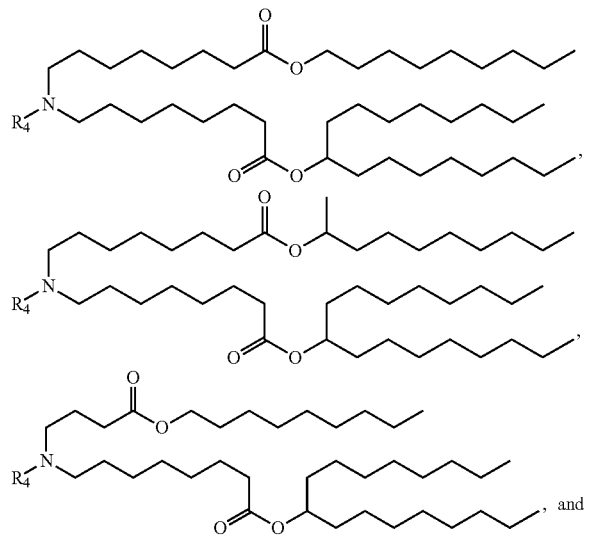

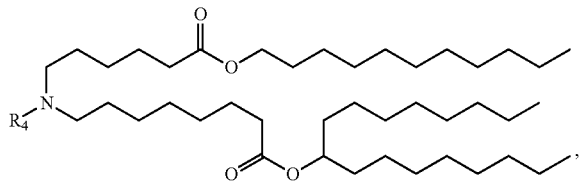

and pharmaceutically acceptable salts thereof. For any one of these four formulas, $R_4$ is independently selected from —$(CH_2)_n Q$ and —$(CH_2)_n CHQR$; Q is selected from the group consisting of —OR, —OH, —O(CH$_2$)$_n$N(R)$_2$, —OC(O)R, —CX$_3$, —CN, —N(R)C(O)R, —N(H)C(O)R, —N(R)S(O)$_2$R, —N(H)S(O)$_2$R, —N(R)C(O)N(R)$_2$, —N(H)C(O)N(R)$_2$, —N(H)C(O)N(H)(R), —N(R)C(S)N(R)$_2$, —N(H)C(S)N(R)$_2$, —N(H)C(S)N(H)(R), and a heterocycle; and n is 1, 2, or 3. In certain embodiments, the compositions and methods of the present invention include a cationic lipid having a compound structure of:

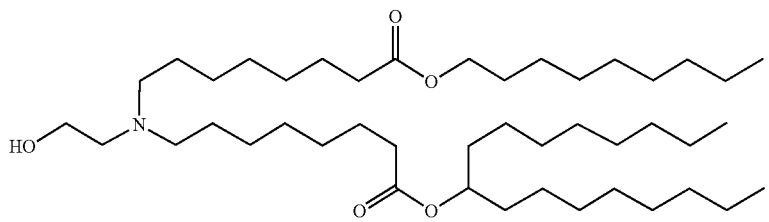 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

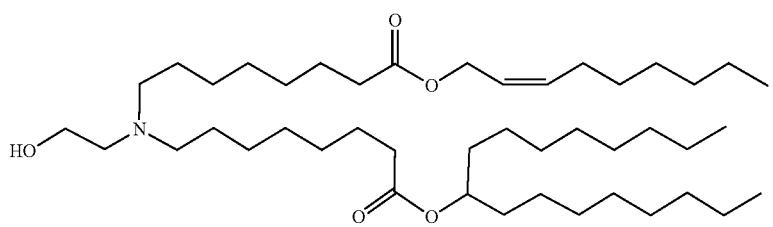 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

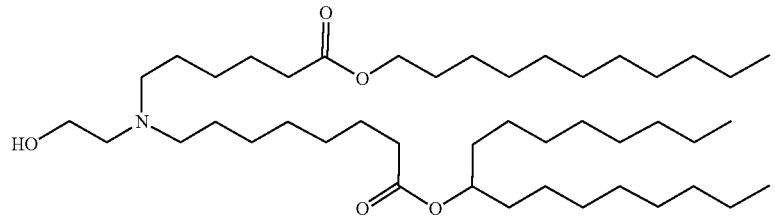 [SMILES: CCCCCCCCCCCOC(=O)CCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

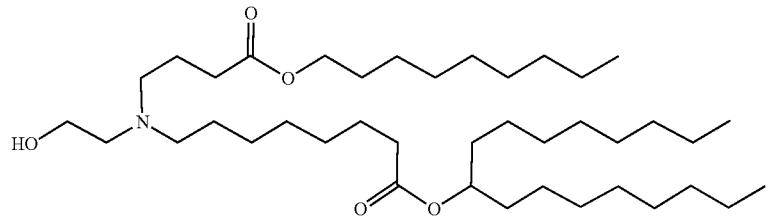 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

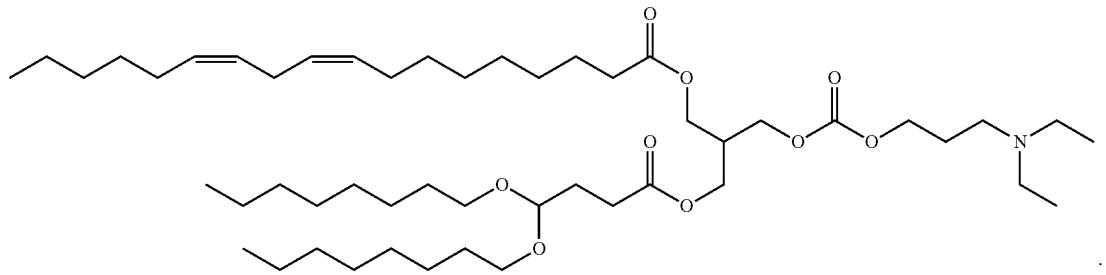 [SMILES: CCCCC/C=C\C/C=C\CCCCCCCC(=O)OCC(COC(=O)CCC(OCCCCCCCC)OCCCCCCCC)COC(=O)OCCCN(CC)CC]

and pharmaceutically acceptable salts thereof. In certain embodiments, the compositions and methods of the present invention include a cationic lipid having a compound structure of:

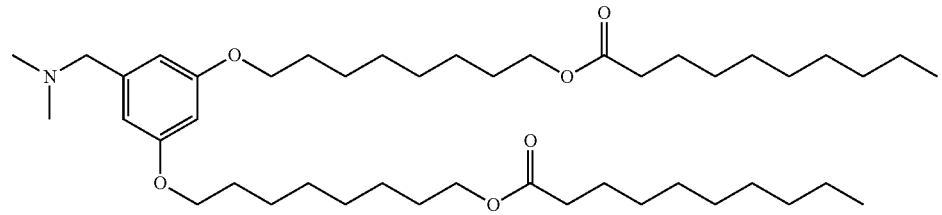 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

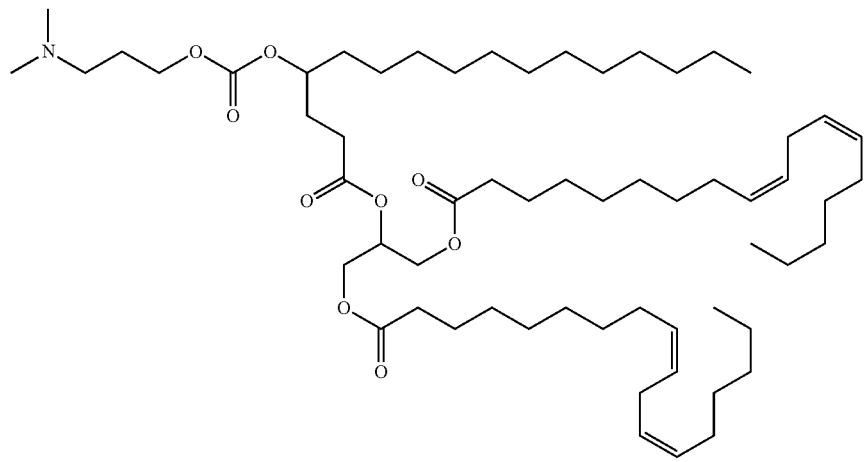 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

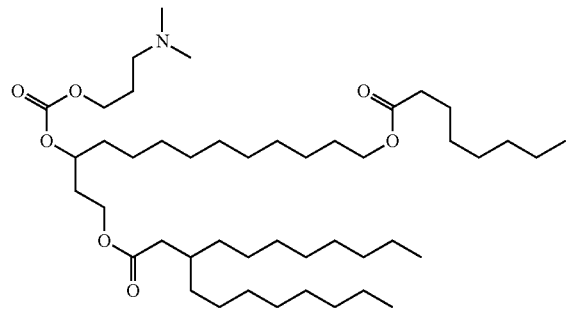 [SMILES: CCCCCCCCC(CCCCCCCC)CC(=O)OCCC(CCCCCCCCCCOC(=O)CCCCCCC)OC(=O)OCCCN(C)C]

and pharmaceutically acceptable salts thereof.

Other suitable cationic lipids for use in the compositions and methods of the invention include cholesterol-based cationic lipids. In certain embodiments, the compositions and methods of the present invention include imidazole cholesterol ester or "ICE", having a compound structure of:

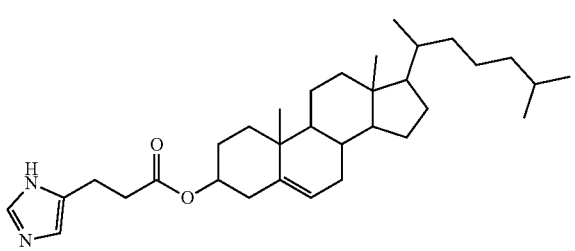

(ICE)

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

$$R_1 \overbrace{\phantom{XXXX}}^{(\phantom{X})_n} S{-}S{\sim}^{R_2},$$

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

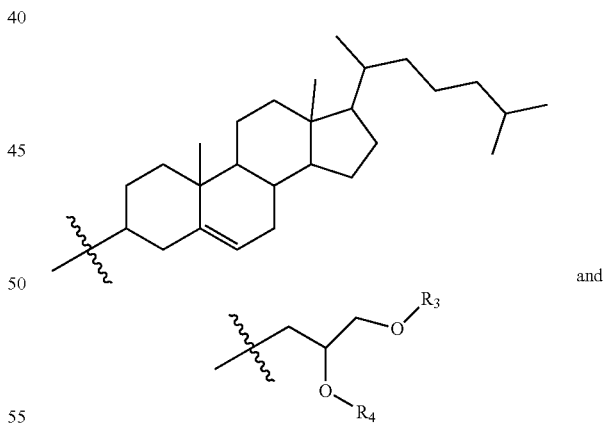

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

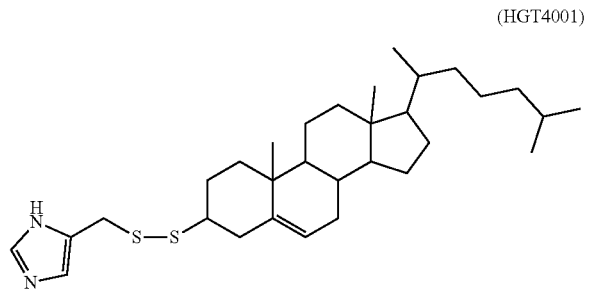 [SMILES: CC(C)CCCC(C)C1CCC2C3CC=C4CC(SSCc5cnc[nH]5)CCC4(C)C3CCC12C]
(HGT4001)

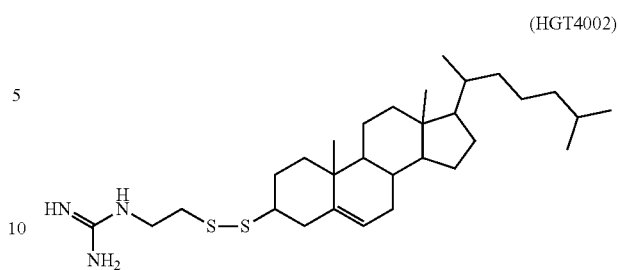
(HGT4002)

and pharmaceutically acceptable salts thereof. In certain embodiments, the compositions and methods of the present invention include a cationic lipid, "HGT4002", having a compound structure of:

and pharmaceutically acceptable salts thereof. In certain embodiments, the compositions and methods of the present invention include a cationic lipid, "HGT4003", having a compound structure of:

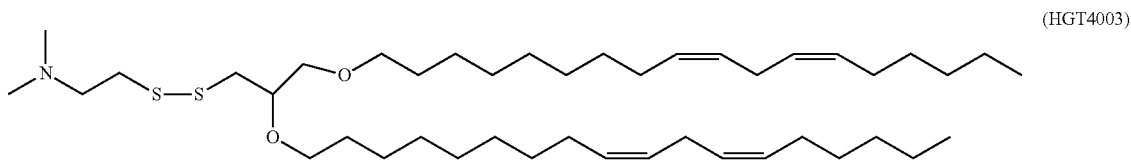 [SMILES: CCCCC/C=C\C/C=C\CCCCCCCCOCC(CSSCCN(C)C)OCCCCCCCC/C=C\C/C=C\CCCCC]
(HGT4003)

and pharmaceutically acceptable salts thereof. In certain embodiments, the compositions and methods of the present invention include a cationic lipid, "HGT4004", having a compound structure of:

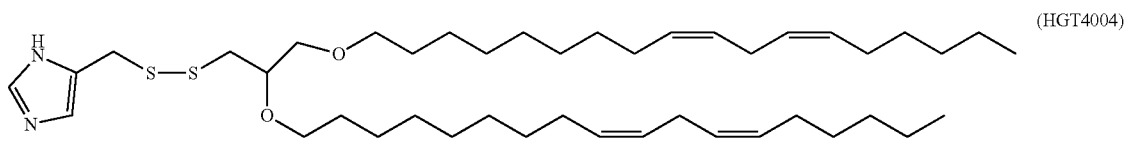 [SMILES: CCCCC/C=C\C/C=C\CCCCCCCCOCC(CSSCc1cnc[nH]1)OCCCCCCCC/C=C\C/C=C\CCCCC]
(HGT4004)

and pharmaceutically acceptable salts thereof. In certain embodiments, the compositions and methods of the present invention include a cationic lipid "HGT4005", having a compound structure of:

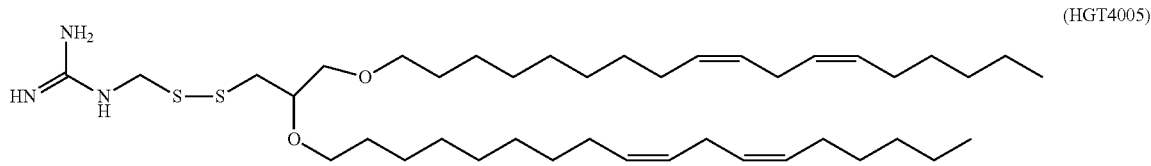 [SMILES: CCCCC/C=C\C/C=C\CCCCCCCCOCC(CSSCNC(=N)N)OCCCCCCCC/C=C\C/C=C\CCCCC]
(HGT4005)

and pharmaceutically acceptable salts thereof.

Other suitable cationic lipids for use in the compositions and methods of the present invention include cleavable cationic lipids as described in U.S. Provisional Application No. 62/672,194, filed May 16, 2018, and incorporated herein by reference. In certain embodiments, the compositions and methods of the present invention include a cationic lipid that is any of general formulas or any of structures (1a)-(21a) and (1b)-(21b) and (22)-(237) described in U.S. Provisional Application No. 62/672,194. In certain embodiments, the compositions and methods of the present invention include a cationic lipid that has a structure according to Formula (I'),

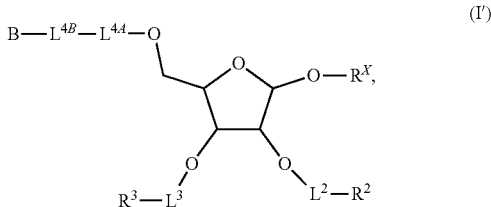

(I')

wherein RX is independently —H, -L1-R1, or -L5A-L5B-B'; each of L1, L2, and L3 is independently a covalent bond, —C(O)—, —C(O)O—, —C(O)S—, or —C(O)NRL-; each L4A and L5A is independently —C(O)—, —C(O)O—, or —C(O)NRL-; each L4B and L5B is independently C1-C20 alkylene; C2-C20 alkenylene; or C2-C20 alkynylene; each B and B' is $NR4R_5$ or a 5- to 10-membered nitrogen-containing heteroaryl; each R1, R2, and R3 is independently C6-C30 alkyl, C6-C30 alkenyl, or C6-C30 alkynyl; each R4 and R5 is independently hydrogen, C1-C10 alkyl; C2-C10 alkenyl; or C2-C10 alkynyl; and each RL is independently hydrogen, C1-C20 alkyl, C2-C20 alkenyl, or C2-C20 alkynyl.

In certain embodiments, the compositions and methods of the present invention include a cationic lipid that is Compound (139) of 62/672,194, having a compound structure of:

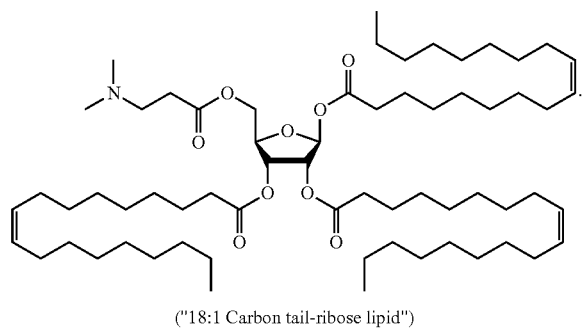

("18:1 Carbon tail-ribose lipid")

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido) ethyl]-N,N-dimethyl-1-propanaminium ("DOSPA") (Behr et al. Proc. Nat.'1 Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylarnrnonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethy 1-1-(cis,cis-9', 1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoyl-carbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N,N-dimethyl-3-[(9Z, 12Z)-octadeca-9, 12-dien-1-yloxy]propane-1-amine ("Octyl-CLinDMA"); (2R)-2-((8-[(3beta)-cholest-5-en-3-yloxy]octyl)oxy)-N, N-dimethyl-3-[(9Z, 12Z)-octadeca-9, 12-dien-1-yloxy]propan-1-amine ("Octyl-CLinDMA (2R)"); (2S)-2-(8-[(3P)-cholest-5-en-3-yloxy]octyl)oxy)-N, fsl-dimethyh3-[(9Z, 12Z)-octadeca-9, 12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z,12Z)-octadeca-9,1 2-dien-1-yl)-1,3-dioxolan-4-yl)-N,N-dimethylethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)-N,N-dimethyl-2,2-di((9Z, 12Z)-octadeca-9,12-dienyl)tetrahydro-3aH-cyclopenta[d] [1,3]dioxol-5-amine ("ALNY-100") and/or 4,7,13-tris(3-oxo-3-(undecylamino)propyl)-N1,N16-diundecyl-4,7,10, 13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, 70%, or 80% measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle.

In some embodiments, sterol-based cationic lipids may be use instead or in addition to cationic lipids described herein. Suitable sterol-based cationic lipids are dialkylamino-, imidazole-, and guanidinium-containing sterol-based cationic lipids. For example, certain embodiments are directed to a composition comprising one or more sterol-based cationic lipids comprising an imidazole, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta [a]phenanthren-3-yl 3-(1H-imidazol-4-yl)propanoate, as represented by structure (I) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta [a]phenanthren-3-yl 3-(1H-imidazol-4-yl)propanoate, as represented by the following structure:

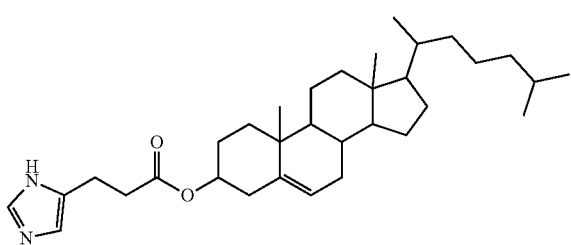

(ICE)

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., ICE lipid) constitutes about 30%, about 35%, about 40%, about 45%, about 50%, about 60%, about 70% or about 80% of the liposome by molar ratio.

Non-Cationic/Helper Lipids

In some embodiments, mRNA-LNPs described herein include non-cationic/helper lipids. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, non-cationic lipids may constitute at least about 5%, 10%, 15%, 20%, 25%, 30%, 35%, 40%, 45%, 50%, 55%, 60%, 65% or 70% of the total lipids by weight or by molar. In some embodiments, non-cationic lipid(s) constitute(s) about 30-50% (e.g., about 30-45%, about 30-40%, about 35-50%, about 35-45%, or about 35-40%) of the total lipids by weight or by molar.

Cholesterol-Based Lipids

In some embodiments, mRNA-LNPs described herein include one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744, 335), or ICE. In some embodiments, cholesterol-based lipid(s) constitute(s) at least about 5%, 10%, 20%, 30%, 40%, 50%, 60%, or 70% of the total lipids by weight or by molar. In some embodiments, cholesterol-based lipid(s) constitute(s) about 30-50% (e.g., about 30-45%, about 30-40%, about 35-50%, about 35-45%, or about 35-40%) of the total lipids by weight or by molar. In some embodiments, cholesterol-based lipid(s) constitute(s) less than about 5%, 10%, 20%, 30%, 40%, 50%, 60%, or 70% of the total lipids by weight or by molar. In some embodiments, mRNA-LNPs described herein do not include cholesterol-based lipids.

PEG-Modified Lipids

In some embodiments, mRNA-LNPs described herein include a low amount (e.g., <0.5% by molar or by weight) of one or more PEG-modified lipids (also known as "PEGylated lipids") or PEG. For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention. Contemplated PEG-modified lipids include, but are not limited to, a polyethylene glycol chain of up to 2 kDa, up to 3 kDa, up to 4 kDa or up to 5 kDa in length covalently attached to a lipid with alkyl chain(s) of C6-C20 length. In some embodiments, a PEG-modified or PEGylated lipid is PEGylated cholesterol or PEG-2K. In some embodiments, particularly useful exchangeable lipids are PEG-ceramides having shorter acyl chains (e.g., $C_{14}$ or $C_{18}$).

In some embodiments, mRNA-LNPs described herein contain less than 0.5%, less than 0.4%, less than 0.3%, less than 0.2% or less than 0.1% of PEG-modified lipids or PEG of the total lipids by molar. In some embodiments, mRNA-LNPs described herein contain less than 0.5%, less than 0.4%, less than 0.3%, less than 0.2% or less than 0.1% of PEG-modified lipids or PEG of the total lipids by weight. In some embodiments, mRNA-LNPs described herein contain 0.4% or less of PEG-modified lipids or PEG, 0.3% or less of PEG-modified lipids or PEG, 0.2% or less of PEG-modified lipids or PEG, or 0.1% or less of PEG-modified lipids or PEG of the total lipids by molar or by weight. In some embodiments, mRNA-LNPs described herein contain 0.09% or less of PEG-modified lipids or PEG of the total lipids by molar or by weight. In some embodiments, mRNA-LNPs described herein contain 0.08% or less of PEG-modified lipids or PEG of the total lipids by molar or by weight. In some embodiments, mRNA-LNPs described herein contain 0.07% or less of PEG-modified lipids or PEG of the total lipids by molar or by weight. In some embodiments, mRNA-LNPs described herein contain 0.06% or less of PEG-modified lipids or PEG of the total lipids by molar or by weight. In some embodiments, mRNA-LNPs described herein contain 0.05% or less of PEG-modified lipids or PEG of the total lipids by molar or by weight. In some embodiments, mRNA-LNPs described herein contain 0.04% or less of PEG-modified lipids or PEG of the total lipids by molar or by weight. In some embodiments, mRNA-LNPs described herein contain 0.03% or less of PEG-modified lipids or PEG of the total lipids by molar or by weight. In some embodiments, mRNA-LNPs described herein contain 0.02% or less of PEG-modified lipids or PEG of the total lipids by molar or by weight. In some embodiments, mRNA-LNPs described herein contain 0.01% or less of PEG-modified lipids or PEG of the total lipids by molar or by weight.

In some embodiments, mRNA-LNPs described herein are substantially free of PEG-modified lipids or PEG.

Amphiphilic Block Copolymers

In some embodiments, mRNA-LNPs described herein contain amphiphilic block copolymers (e.g., poloxamers). In some embodiments, mRNA-LNPs comprise less than 5% amphiphilic block copolymers (e.g., poloxamers). In some embodiments, mRNA-LNPs comprise less than 3% amphiphilic block copolymers (e.g., poloxamers). In some embodiments, mRNA-LNPs comprise less than 2.5% amphiphilic block copolymers (e.g., poloxamers). In some embodiments, mRNA-LNPs comprise less than 2% amphiphilic block copolymers (e.g., poloxamers). In some embodiments, mRNA-LNPs comprise less than 1.5% amphiphilic block copolymers (e.g., poloxamers). In some embodiments, mRNA-LNPs comprises less than 1% amphiphilic block copolymers (e.g., poloxamers). In some embodiments, mRNA-LNPs comprise less than 0.5% (e.g., less than 0.4%, 0.3%, 0.2%, 0.1%) amphiphilic block copolymers (e.g., poloxamers). In some embodiments, mRNA-LNPs comprise less than 0.09%, 0.08%, 0.07%, 0.06%, 0.05%, 0.04%, 0.03%, 0.02%, or 0.01% amphiphilic block copolymers (e.g., poloxamers). In some embodiments, mRNA-LNPs comprise less than 0.01% amphiphilic block copolymers (e.g., poloxamers). In some embodiments, mRNA-LNPs contain a residual amount of amphiphilic polymers (e.g., poloxamers). As used herein, a residual amount means a remaining amount after substantially all of the substance (an amphiphilic polymer described herein such as a poloxamer) in a composition is removed. A residual amount may be detectable using a known technique qualitatively or quantitatively. A residual amount may not be detectable using a known technique.

Messenger RNA (mRNA)

The present invention may be used to encapsulate any mRNA. mRNA is typically thought of as the type of RNA that carries information from DNA to the ribosome. Typically, in eukaryotic organisms, mRNA processing comprises the addition of a "cap" on the 5' end, and a "tail" on the 3' end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The additional of a tail is typically a polyadenylation event whereby a polyadenylyl moiety is added to the 3' end of the mRNA molecule. The presence of this "tail" serves to protect the mRNA from exonuclease degradation. Messenger RNA is translated by the ribosomes into a series of amino acids that make up a protein.

mRNAs may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNase I, pyrophosphatase, and/or RNAse inhibitor. The exact conditions will vary according to the specific application.

In some embodiments, in vitro synthesized mRNA may be purified before formulation and encapsulation to remove undesirable impurities including various enzymes and other reagents used during mRNA synthesis.

The present invention may be used to formulate and encapsulate mRNAs of a variety of lengths. In some embodiments, the present invention may be used to formulate and encapsulate in vitro synthesized mRNA of or greater than about 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, or 20 kb in length. In some embodiments, the present invention may be used to formulate and encapsulate in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length.

The present invention may be used to formulate and encapsulate mRNA that is unmodified or mRNA containing one or more modifications that typically enhance stability. In some embodiments, modifications are selected from modified nucleotides, modified sugar phosphate backbones, and 5' and/or 3' untranslated region.

In some embodiments, modifications of mRNA may include modifications of the nucleotides of the RNA. A modified mRNA according to the invention can include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydrouracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine, pseudouridine, 5-methylcytidine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

Typically, mRNA synthesis includes the addition of a "cap" on the 5' end, and a "tail" on the 3' end. The presence of the cap is important in providing resistance to nucleases found in most eukaryotic cells. The presence of a "tail" serves to protect the mRNA from exonuclease degradation.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. 2'-O-methylation may also occur at the first base and/or second base following the 7-methyl guanosine triphosphate residues. Examples of cap structures include, but are not limited to, m7GpppNp-RNA, m7GpppNmp-RNA and m7GpppNmpNmp-RNA (where m indicates 2'-Omethyl residues).

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

While mRNA provided from in vitro transcription reactions may be desirable in some embodiments, other sources of mRNA are contemplated as within the scope of the invention including mRNA produced from bacteria, fungi, plants, and/or animals.

The present invention may be used to formulate and encapsulate mRNAs encoding a variety of proteins. Non-limiting examples of mRNAs suitable for the present invention include mRNAs encoding erythropoietin (EPO) and firefly luciferase (FFL).

Formulations

Various formulations may be used in connection with the present invention. In some embodiments, a suitable formulation solution may include a buffering agent or salt. Exemplary buffering agent may include HEPES, ammonium sulfate, sodium bicarbonate, sodium citrate, sodium acetate, potassium phosphate and sodium phosphate. Exemplary salt may include sodium chloride, magnesium chloride, and potassium chloride.

In some embodiments, a suitable formulation solution is an aqueous solution comprising pharmaceutically acceptable excipients, including, but not limited to, a cryoprotectant. In some embodiments, a suitable formulation solution is an aqueous solution comprising pharmaceutically acceptable excipients, including, but not limited to, sugar, such as one or more of trehalose, sucrose, mannose, lactose, and mannitol. In some embodiments, a suitable formulation solution comprises trehalose. In some embodiments, a suitable formulation solution comprises sucrose. In some embodiments, a suitable formulation solution comprises mannose. In some embodiments, a suitable formulation solution comprises lactose. In some embodiments, a suitable formulation solution comprises mannitol.

In some embodiments, a suitable formulation solution is an aqueous solution comprising 5% to 20% weight to volume of a sugar, such as of trehalose, sucrose, mannose, lactose, and mannitol. In some embodiments, a suitable formulation solution is an aqueous solution comprising 5% to 20% weight to volume of trehalose. In some embodiments, a suitable formulation solution is an aqueous solution comprising 5% to 20% weight to volume of sucrose. In some embodiments, a suitable formulation solution is an aqueous solution comprising 5% to 20% weight to volume of mannose. In some embodiments, a suitable formulation solution is an aqueous solution comprising 5% to 20% weight to volume of lactose. In some embodiments, a suitable formulation solution is an aqueous solution comprising 5% to 20% weight to volume of mannitol.

In some embodiments, a suitable formulation solution is an aqueous solution comprising about 10% weight to volume of a sugar, such as of trehalose, sucrose, mannose, lactose, and mannitol. In some embodiments, a suitable formulation solution is an aqueous solution comprising about 10% weight to volume of trehalose. In some embodiments, a suitable formulation solution is an aqueous solution comprising about 10% weight to volume of sucrose. In some embodiments, a suitable formulation solution is an aqueous solution comprising about 10% weight to volume of mannose. In some embodiments, a suitable formulation solution is an aqueous solution comprising about 10% weight to volume of lactose. In some embodiments, a suitable formulation solution is an aqueous solution comprising about 10% weight to volume of mannitol.

In some embodiments, one or both of a non-aqueous solvent, such as ethanol, and citrate are absent from the drug product formulation solution. In some embodiments, a suitable formulation solution includes only residual citrate. In some embodiments, a suitable formulation solution includes only residual non-aqueous solvent, such as ethanol. In some embodiments, a suitable formulation solution contains less than about 10 mM (e.g., less than about 9 mM, about 8 mM, about 7 mM, about 6 mM, about 5 mM, about 4 mM, about 3 mM, about 2 mM, or about 1 mM) of citrate. In some embodiments, a suitable formulation solution contains less than about 25% (e.g., less than about 20%, about 15%, about 10%, about 5%, about 4%, about 3%, about 2%, or about 1%) of non-aqueous solvents, such as ethanol. In some embodiments, a suitable formulation solution does not require any further downstream processing (e.g., buffer exchange and/or further purification steps and/or additional excipients) prior to lyophilization. In some embodiments, a suitable formulation solution does not require any further downstream processing (e.g., buffer exchange and/or further purification steps and/or additional excipients) prior to administration to a sterile fill into a vial, syringe or other vessel. In some embodiments, a suitable formulation solution does not require any further downstream processing (e.g., buffer exchange and/or further purification steps and/or additional excipients) prior to administration to a subject.

In some embodiments, a suitable formulation solution has a pH between pH 4.5 and pH 7.5. In some embodiments, a suitable formulation solution has a pH between pH 5.0 and pH 7.0. In some embodiments, a suitable formulation solution has a pH between pH 5.5 and pH 7.0. In some embodiments, a suitable formulation solution has a pH above pH 4.5. In some embodiments, a suitable formulation solution has a pH above pH 5.0. In some embodiments, a suitable formulation solution has a pH above pH 5.5. In some embodiments, a suitable formulation solution has a pH above pH 6.0. In some embodiments, a suitable formulation solution has a pH above pH 6.5.

In some embodiments, the improved or enhanced amount of encapsulation of mRNA-LNPs in a suitable formulation solution following heating is retained after subsequent freeze-thaw of the drug product formulation solution. In some embodiments, a suitable formulation solution is 10% trehalose and can be stably frozen.

In some embodiments, mRNA-LNPs in a suitable formulation solution following heating can be stably frozen (e.g., retain enhanced encapsulation) in about 5%, about 10%, about 15%, about 20%, about 25%, about 30%, about 35%, about 40%, about 45%, or about 50% trehalose solution. In some embodiments, a suitable formulation solution does not require any downstream purification or processing and can be stably stored in frozen form.

Therapeutic Uses

In certain embodiments the present invention provides a method for producing a therapeutic composition comprising mRNA-LNPs described herein that encode a peptide or polypeptide for use in the delivery to or treatment of a human subject. In some embodiments, a therapeutic composition comprising mRNA-LNPs described herein is used for delivery in the lung of a subject or a lung cell. In certain embodiments, the present invention provides a method for producing a therapeutic composition comprising mRNA-LNPs described herein that deliver an endogenous protein which may be deficient or non-functional in a subject.

In certain embodiments, the present invention provides a method for producing a therapeutic composition comprising mRNA-LNPs described herein that deliver a peptide or polypeptide for use in the treatment of a lung disease. In certain embodiments, the present invention is useful in a method for manufacturing mRNA encoding cystic fibrosis transmembrane conductance regulator, CFTR. The CFTR mRNA is delivered to the lung of a subject in need in a therapeutic composition for treating cystic fibrosis. In certain embodiments, the present invention provides a method for producing a therapeutic composition comprising mRNA-LNPs described herein that deliver a peptide or polypeptide for use in the treatment of a liver disease or metabolic disease. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methyl malonic acidemia, or associated with any other metabolic disorder for which delivery to or treatment of the liver or a liver cell with enriched full-length mRNA provides therapeutic benefit.

In certain embodiments the present invention provides a method for producing a therapeutic composition comprising mRNA-LNPs described herein that deliver a protein associated with a urea cycle disorder. In certain embodiments, the present invention provides a method for producing a therapeutic composition comprising mRNA-LNPs described herein that deliver an ornithine transcarbamylase (OTC) protein. In certain embodiments, the present invention provides a method for producing a therapeutic composition comprising mRNA-LNPs described herein that deliver an arginosuccinate synthetase 1 protein. In certain embodiments the present invention provides a method for producing a therapeutic composition comprising mRNA-LNPs described herein that deliver carbamoyl phosphate synthetase I protein. In certain embodiments the present invention provides a method for producing a therapeutic composition comprising mRNA-LNPs described herein that deliver an arginosuccinate lyase protein. In certain embodiments, the present invention provides a method for producing a therapeutic composition comprising mRNA-LNPs described herein that deliver an arginase protein.

In certain embodiments the present invention provides a method for producing a therapeutic composition comprising mRNA-LNPs described herein that deliver a protein associated with a lysosomal storage disorder. In certain embodiments the present invention provides a method for producing a therapeutic composition comprising mRNA-LNPs described herein that deliver an alpha galactosidase protein. In certain embodiments the present invention provides a method for producing a therapeutic composition comprising mRNA-LNPs described herein that deliver a glucocerebrosidase protein. In certain embodiments the present invention provides a method for producing a therapeutic composition comprising mRNA-LNPs described herein that deliver iduronate-2-sulfatase protein. In certain embodiments the present invention provides a method for producing a therapeutic composition comprising mRNA-LNPs described herein that deliver iduronidase protein. In certain embodiments the present invention provides a method for producing a therapeutic composition comprising mRNA-LNPs described herein that deliver N-acetyl-alpha-D-glucosaminidase protein. In certain embodiments the present invention provides a method for producing a therapeutic composition comprising mRNA-LNPs described herein that deliver heparan N-sulfatase protein. In certain embodiments the present invention provides a method for producing a therapeutic composition comprising mRNA-LNPs described herein that deliver galactosamine-6 sulfatase protein. In certain embodiments the present invention provides a method for producing a therapeutic composition comprising mRNA-LNPs described herein that deliver beta-galactosidase protein. In certain embodiments the present invention provides a method for producing a therapeutic composition comprising mRNA-LNPs described herein that deliver lysosomal lipase protein. In certain embodiments, the present invention provides a method for producing a therapeutic composition comprising mRNA-LNPs described herein that deliver an arylsulfatase B (N-acetylgalactosamine-4-sulfatase) protein. In certain embodiments, the present invention provides a method for producing a therapeutic composition comprising mRNA-LNPs described herein that deliver transcription factor EB (TFEB).

In certain embodiments the present invention provides a method for producing a therapeutic composition comprising mRNA-LNPs described herein that deliver a protein associated with a glycogen storage disorder. In certain embodiments the present invention provides a method for producing a therapeutic composition comprising mRNA-LNPs described herein that deliver acid alpha-glucosidase protein. In certain embodiments the present invention provides a method for producing a therapeutic composition comprising mRNA-LNPs described herein that deliver glucose-6-phosphatase (G6PC) protein. In certain embodiments the present invention provides a method for producing a therapeutic composition comprising mRNA-LNPs described herein that deliver liver glycogen phosphorylase protein. In certain embodiments the present invention provides a method for producing a therapeutic composition comprising mRNA-LNPs described herein that deliver muscle phosphoglycerate mutase protein. In certain embodiments the present invention provides a method for producing a therapeutic composition comprising mRNA-LNPs described herein that deliver glycogen debranching enzyme.

In certain embodiments the present invention provides a method for producing a therapeutic composition comprising mRNA-LNPs described herein that deliver a protein associated with amino acid metabolism. In certain embodiments the present invention provides a method for producing a therapeutic composition comprising mRNA-LNPs described herein that deliver phenylalanine hydroxylase enzyme. In certain embodiments the present invention provides a method for producing a therapeutic composition comprising mRNA-LNPs described herein that deliver glutaryl-CoA dehydrogenase enzyme. In certain embodiments the present invention provides a method for producing a therapeutic composition comprising mRNA-LNPs described herein that deliver propionyl-CoA caboxylase enzyme. In certain embodiments, the present invention provides a method for producing a therapeutic composition comprising mRNA-LNPs described herein that deliver oxalase alanine-glyoxylate aminotransferase enzyme.

In certain embodiments, the present invention provides a method for producing a therapeutic composition comprising mRNA-LNPs described herein that deliver a protein associated with a lipid metabolism or fibrotic disorder. In certain embodiments the present invention provides a method for producing a therapeutic composition comprising mRNA-LNPs described herein that deliver an mTOR inhibitor. In certain embodiments the present invention provides a method for producing a therapeutic composition comprising mRNA-LNPs described herein that deliver ATPase phospholipid transporting 8B1 (ATP8B1) protein. In certain embodiments the present invention provides a method for producing a therapeutic composition comprising mRNA-LNPs described herein that deliver one or more NF-kappa B inhibitors, such as one or more of I-kappa B alpha, interferon-related development regulator 1 (IFRD1), and Sirtuin 1 (SIRT1). In certain embodiments, the present invention provides a method for producing a therapeutic composition comprising mRNA-LNPs described herein that deliver PPAR-gamma protein or an active variant.

In certain embodiments, the present invention provides a method for producing a therapeutic composition comprising mRNA-LNPs described herein that deliver a protein associated with methyl malonic acidemia. For example, in certain embodiments the present invention provides a method for producing a therapeutic composition comprising mRNA-LNPs described herein that deliver methyl malonyl CoA mutase protein. In certain embodiments, the present invention provides a method for producing a therapeutic composition comprising mRNA-LNPs described herein that deliver methylmalonyl CoA epimerase protein.

In certain embodiments, the present invention provides a method for producing a therapeutic composition comprising mRNA-LNPs described herein that deliver a peptide or polypeptide for use in the delivery to or treatment of the liver. In certain embodiments, the present invention provides a method for producing a therapeutic composition comprising mRNA-LNPs described herein that deliver ATP7B protein, also known as Wilson disease protein. In certain embodiments, the present invention provides a method for producing a therapeutic composition comprising mRNA-LNPs described herein that deliver porphobilinogen deaminase enzyme. In certain embodiments the present invention provides a method for producing a therapeutic composition comprising mRNA-LNPs described herein that deliver one or clotting enzymes, such as Factor VIII, Factor IX, Factor VII, and Factor X. In certain embodiments, the present invention provides a method for producing a therapeutic composition comprising mRNA-LNPs described herein that deliver human hemochromatosis (HFE) protein.

In certain embodiments, the present invention provides a method for producing a therapeutic composition comprising mRNA-LNPs described herein that deliver a peptide or polypeptide for use in the delivery to or treatment of the cardiovascular conditions of a subject or a cardiovascular cell. In certain embodiments, the present invention provides a method for producing a therapeutic composition comprising mRNA-LNPs described herein that deliver vascular endothelial growth factor A protein. In certain embodiments, the present invention provides a method for producing a therapeutic composition comprising mRNA-LNPs described herein that deliver relaxin protein. In certain embodiments, the present invention provides a method for producing a therapeutic composition comprising mRNA-LNPs described herein that deliver bone morphogenetic protein-9 protein. In certain embodiments, the present invention provides a method for producing a therapeutic composition comprising p mRNA-LNPs described herein that deliver bone morphogenetic protein-2 receptor protein.

In certain embodiments, the present invention provides a method for producing a therapeutic composition comprising mRNA-LNPs described herein that deliver a peptide or polypeptide for use in the delivery to or treatment of the muscle of a subject or a muscle cell. In certain embodiments, the present invention provides a method for producing a therapeutic composition comprising mRNA-LNPs described herein that deliver dystrophin protein. In certain embodiments, the present invention provides a method for producing a therapeutic composition comprising mRNA-LNPs described herein that deliver frataxin protein. In certain embodiments, the present invention provides a method for producing a therapeutic composition comprising mRNA-LNPs described herein that deliver a peptide or polypeptide for use in the delivery to or treatment of the cardiac muscle of a subject or a cardiac muscle cell. In certain embodiments, the present invention provides a method for producing a therapeutic composition comprising mRNA-LNPs described herein that deliver a protein that modulates one or both of a potassium channel and a sodium channel in muscle tissue or in a muscle cell. In certain embodiments the present invention provides a method for producing a therapeutic composition comprising mRNA-LNPs described herein that deliver a protein that modulates a Kv7.1 channel in muscle tissue or in a muscle cell. In certain embodiments, the present invention provides a method for producing a therapeutic composition comprising mRNA-LNPs described herein that deliver a protein that modulates a Nav1.5 channel in muscle tissue or in a muscle cell.

In certain embodiments, the present invention provides a method for producing a therapeutic composition comprising mRNA-LNPs described herein that deliver a peptide or polypeptide for use in the delivery to or treatment of the nervous system of a subject or a nervous system cell. For example, in certain embodiments the present invention provides a method for producing a therapeutic composition comprising mRNA-LNPs described herein that deliver survival motor neuron 1 protein. For example, in certain embodiments the present invention provides a method for producing a therapeutic composition comprising mRNA-LNPs described herein that deliver survival motor neuron 2 protein. In certain embodiments, the present invention provides a method for producing a therapeutic composition comprising mRNA-LNPs described herein that deliver frataxin protein. In certain embodiments, the present invention provides a method for producing a therapeutic composition comprising mRNA-LNPs described herein that deliver ATP binding cassette subfamily D member 1 (ABCD1) protein. In certain embodiments, the present invention provides a method for producing a therapeutic composition comprising mRNA-LNPs described herein that deliver CLN3 protein.

In certain embodiments, the present invention provides a method for producing a therapeutic composition comprising mRNA-LNPs described herein that deliver a peptide or polypeptide for use in the delivery to or treatment of the blood or bone marrow of a subject or a blood or bone marrow cell. In certain embodiments, the present invention provides a method for producing a therapeutic composition comprising mRNA-LNPs described herein that deliver beta globin protein. In certain embodiments, the present invention provides a method for producing a therapeutic composition comprising mRNA-LNPs described herein that deliver Bruton's tyrosine kinase protein. In certain embodiments, the present invention provides a method for producing a therapeutic composition comprising mRNA-LNPs described herein that deliver one or clotting enzymes, such as Factor VIII, Factor IX, Factor VII, and Factor X.

In certain embodiments, the present invention provides a method for producing a therapeutic composition comprising mRNA-LNPs described herein that deliver a peptide or polypeptide for use in the delivery to or treatment of the kidney of a subject or a kidney cell. In certain embodiments, the present invention provides a method for producing a therapeutic composition comprising mRNA-LNPs described herein that deliver collagen type IV alpha 5 chain (COL4A5) protein.

In certain embodiments, the present invention provides a method for producing a therapeutic composition comprising mRNA-LNPs described herein that deliver a peptide or polypeptide for use in the delivery to or treatment of the eye of a subject or an eye cell. In certain embodiments, the present invention provides a method for producing a therapeutic composition comprising mRNA-LNPs described herein that deliver ATP-binding cassette sub-family A member 4 (ABCA4) protein. In certain embodiments, the present invention provides a method for producing a therapeutic composition comprising mRNA-LNPs described herein that deliver retinoschisin protein. In certain embodiments, the present invention provides a method for producing a therapeutic composition comprising mRNA-LNPs described herein that deliver retinal pigment epithelium-specific 65 kDa (RPE65) protein. In certain embodiments, the present invention provides a method for producing a therapeutic composition comprising mRNA-LNPs described herein that deliver centrosomal protein of 290 kDa (CEP290).

In certain embodiments, the present invention provides a method for producing a therapeutic composition comprising mRNA-LNPs described herein that deliver s a peptide or polypeptide for use in the delivery of or treatment with a vaccine for a subject or a cell of a subject. For example, in certain embodiments the present invention provides a method for producing a therapeutic composition comprising mRNA-LNPs described herein that deliver an antigen from an infectious agent, such as a virus. In certain embodiments, the present invention provides a method for producing a therapeutic composition comprising mRNA-LNPs described herein that deliver an antigen from influenza virus. In certain embodiments, the present invention provides a method for producing a therapeutic composition comprising mRNA-LNPs described herein that deliver an antigen from respiratory syncytial virus. In certain embodiments, the present invention provides a method for producing a therapeutic composition comprising mRNA-LNPs described herein that deliver an antigen from rabies virus. In certain embodiments, the present invention provides a method for producing a therapeutic composition comprising mRNA-LNPs described herein that deliver an antigen from cytomegalovirus. In certain embodiments, the present invention provides a method for producing a therapeutic composition comprising mRNA-LNPs described herein that deliver an antigen from rotavirus. In certain embodiments, the present invention provides a method for producing a therapeutic composition comprising mRNA-LNPs described herein that deliver an antigen from a hepatitis virus, such as hepatitis A virus, hepatitis B virus, or hepatitis C virus. In certain embodiments, the present invention provides a method for producing a therapeutic composition comprising mRNA-LNPs described herein that deliver an antigen from human papillomavirus. In certain embodiments, the present invention provides a method for producing a therapeutic composition comprising mRNA-LNPs described herein that deliver an antigen from a herpes simplex virus, such as herpes simplex virus 1 or herpes simplex virus 2. In certain embodiments, the present invention provides a method for producing a therapeutic composition comprising mRNA-LNPs described herein that deliver an antigen from a human immunodeficiency virus, such as human immunodeficiency virus type 1 or human immunodeficiency virus type 2. In certain embodiments, the present invention provides a method for producing a therapeutic composition comprising mRNA-LNPs described herein that deliver an antigen from a human metapneumovirus. In certain embodiments, the present invention provides a method for producing a therapeutic composition comprising mRNA-LNPs described herein that deliver an antigen from a human parainfluenza virus, such as human parainfluenza virus type 1, human parainfluenza virus type 2, or human parainfluenza virus type 3. In certain embodiments, the present invention provides a method for producing a therapeutic composition comprising mRNA-LNPs described herein that deliver an antigen from malaria virus. In certain embodiments, the present invention provides a method for producing a therapeutic composition comprising mRNA-LNPs described herein that deliver an antigen from zika virus. In certain embodiments, the present invention provides a method for producing a therapeutic composition comprising mRNA-LNPs described herein that deliver an antigen from chikungunya virus.

In certain embodiments, the present invention provides a method for producing a therapeutic composition comprising mRNA-LNPs described herein that deliver an antigen associated with a cancer of a subject or identified from a cancer cell of a subject. In certain embodiments, the present invention provides a method for producing a therapeutic composition comprising mRNA-LNPs described herein that deliver an antigen determined from a subject's own cancer cell, i.e., to provide a personalized cancer vaccine. In certain embodiments, the present invention provides a method for producing a therapeutic composition comprising mRNA-LNPs described herein that deliver an antigen expressed from a mutant KRAS gene.

In certain embodiments, the present invention provides a method for producing a therapeutic composition comprising mRNA-LNPs described herein that deliver an antibody. In certain embodiments, the antibody can be a bi-specific antibody. In certain embodiments, the antibody can be part of a fusion protein. In some embodiments, two separate mRNA-LNPs in step (b) of the process comprise mRNA encoding a light chain and heavy chain of an antibody. In some embodiments, the mRNA-LNP composition of the invention may comprise a combination of non-identical LNPs comprising different lipid composition, and encapsulating mRNA encoding a light chain or a heavy chain of an antibody. In certain embodiments, the present invention provides a method for producing a therapeutic composition comprising mRNA-LNPs described herein that deliver an antibody to OX40. In certain embodiments, the present invention provides a method for producing a therapeutic composition comprising mRNA-LNPs described herein that deliver an antibody to VEGF. In certain embodiments, the present invention provides a method for producing a therapeutic composition comprising mRNA-LNPs described herein that deliver an antibody to tissue necrosis factor alpha. In certain embodiments the present invention provides a method for producing a therapeutic composition comprising mRNA-LNPs described herein that deliver an antibody to CD3. In certain embodiments the present invention provides a method for producing a therapeutic composition comprising mRNA-LNPs described herein that deliver an antibody to CD19.

In certain embodiments, the present invention provides a method for producing a therapeutic composition comprising mRNA-LNPs described herein that deliver an immunomodulator. In certain embodiments, the present invention provides a method for producing a therapeutic composition comprising mRNA-LNPs described herein that deliver Interleukin 12. In certain embodiments, the present invention provides a method for producing a therapeutic composition comprising mRNA-LNPs described herein that deliver Interleukin 23. In certain embodiments, the present invention provides a method for producing a therapeutic composition comprising mRNA-LNPs described herein that deliver Interleukin 36 gamma. In certain embodiments, the present invention provides a method for producing a therapeutic composition comprising mRNA-LNPs described herein that deliver a constitutively active variant of one or more stimulator of interferon genes (STING) proteins.

In certain embodiments, the present invention provides a method for producing a therapeutic composition comprising mRNA-LNPs described herein that deliver an endonuclease. In certain embodiments, the present invention provides a method for producing a therapeutic composition comprising mRNA-LNPs described herein that deliver an RNA-guided DNA endonuclease protein, such as Cas 9 protein. In certain embodiments, the present invention provides a method for producing a therapeutic composition comprising mRNA-LNPs described herein that deliver a meganuclease protein. In certain embodiments, the present invention provides a method for producing a therapeutic composition comprising mRNA-LNPs described herein that deliver a transcription activator-like effector nuclease protein. In certain embodiments, the present invention provides a method for producing a therapeutic composition comprising mRNA-LNPs described herein that deliver a zinc finger nuclease protein.

In certain embodiments, the present invention provides a method for producing a therapeutic composition comprising mRNA-LNPs described herein that deliver a peptide or protein to treat an ocular disease. In some embodiments, the method is used for producing a therapeutic composition comprising mRNA-LNPs described herein that deliver retinoschisin.

EXAMPLES

While certain compounds, compositions and methods of the present invention have been described with specificity in accordance with certain embodiments, the following example serve only to illustrate the invention and are not intended to limit the same.

Example 1. Encapsulation of mRNA within Lipid Nanoparticles Comprising Low or No PEG-Modified Lipids Using Poloxamer This example illustrates an exemplary process of encapsulating mRNA within a lipid nanoparticles with low or no PEG-modified lipids by applying Process A. As used herein, Process A refers to a conventional method of encapsulating mRNA by mixing mRNA with a mixture of lipids, e.g., without first pre-forming the lipids into lipid nanoparticles, as described in Published U.S. Patent Application Serial No. US2018/0008680, the entirety of which is incorporated by reference.

An exemplary formulation Process is shown in FIG. 1. In this process, a lipid solution (e.g., in ethanol) and an aqueous solution comprising mRNA and poloxamer were prepared separately. In particular, the lipid solution (cationic lipid, helper lipids, zwitterionic lipids, PEG-modified lipids etc.) was prepared by dissolving lipids in ethanol. The aqueous solution was prepared by dissolving the mRNA and poloxamer in citrate buffer. Then, these two solutions were mixed using a pump system to provide mRNA-encapsulated LNPs. It is worth-noting that it is desirable to keep the amount of poloxamer in the mixture below its critical micelle concentration (CMC) to prevent precipitation. The LNP formation solution comprising mRNA-LNPs was then dialyzed against solution comprising 10% trehalose to remove extra mRNA and poloxamer at room temperature for few hours and then at 4° C. overnight. Following the dialysis, the mRNA-loaded formulation solution was concentrated and stored for subsequent analysis.

Five different LNP formulations were made by the above-described encapsulation process and analyzed as shown in Table 1 below.

TABLE 1 mRNA-LNPs with various amount of PEG-modified lipid and Poloxamer

| Formulation | PEG-modified Lipid | Poloxamer included during encapsulation process | Size (nm) | PDI | Encapsulation Efficiency % |
|---|---|---|---|---|---|
| 1 | 0.0% | 0.5% | 124 | 0.177 | 54 |
| 2 | 0.2% | 0.5% | 123 | 0.186 | 58 |
| 3 | 0.4% | 0.5% | 109 | 0.165 | 59 |
| 4 | 0.0% | 0.0% | n/a | n/a | n/a |
| 5 | 0.4% | 0.0% | 337 | 0.069 | 92 |

The stable LNPs without both PEG-modified lipids and poloxamer could not be formed as the formulation solution crashed and precipitated (Table 1, Formulation 4). In the absence of poloxamer, the LNP with low PEG-modified lipids (e.g., 0.4%) had a large particle size of 337 nm (Table 1, Formulation 5). When 0.5% poloxamer was used during the encapsulation process as described above, surprisingly, the size of LNPs decreased significantly, by factor of 3. (Table 1, Formulations 1-3). Furthermore, the stable LNPs could be formed even in the absence of PEG-modified lipid (Table 1, Formulation 1).

This example demonstrates that inclusion of poloxamer during an encapsulation process resulted in stable mRNA-LNPs containing low or no PEG-modified lipids. Significantly, poloxamer shielding significantly reduced the sizes of LNPs, resulting in mRNA-LNPs with low or no PEG-modified lipids with sizes less than 200 nm particularly suitable for therapeutic use.

Example 2. Post LNP Formation Heating Increased Encapsulation Efficiency of LNPs This example illustrates that an additional step of heating mRNA-LNPs post-formation increases the encapsulation efficiency.

Specifically, following the encapsulation of mRNA into LNPs by Process A as described above, the resultant mRNA-LNPs formulation solution was heated to above ambient temperature. Following heating, the mRNA-LNPs solution was cooled and stored for subsequent analysis. For each formulation, the size, PDI, and encapsulation efficiency were measured before and after heating.

TABLE 2

Effect of the heating step post mRNA-LNP formation

| Formulation | PEG-modified Lipid | Poloxamer included during encapsulation process | No Heating after mRNA-LNP formation | | | Heating after mRNA-LNP formation | | |
|---|---|---|---|---|---|---|---|---|
| | | | Size (nm) | PDI | EE % | Size (nm) | PDI | EE % |
| 1 | 0.0% | 0.5% | 121 | 0.202 | 66 | 124 | 0.177 | 54 |
| 2 | 0.2% | 0.5% | 122 | 0.195 | 32 | 123 | 0.186 | 58 |
| 3 | 0.4% | 0.5% | 110 | 0.180 | 47 | 109 | 0.165 | 59 |

As shown in Table 2, the encapsulation efficiency (EE %) of formulations 2 and 3, which comprise 0.2% and 0.4% of PEG-modified lipid, respectively, were significantly increased following a post-formation heating step as compared to the encapsulation efficiency of the same formulation prior to the heating. The PDI of all formulations tested decreased slightly, and the particle size remained relatively constant.

Example 3. mRNA-LNPs are Stable after Multiple Freeze/Thaw Cycles

This example illustrates that the mRNA-loaded LNPs made according to the present invention are stable after multiple freeze/thaw cycles.

Specifically, three different LNP formulations with varying PEG-modified lipid and poloxamer were made by the above-described encapsulation process. For each formulation, the size and encapsulation efficiency were measured before and after freeze/thaw cycles.

TABLE 3

Stable mRNA-LNPs after Freeze/Thaw Cycles

| Formulation | PEG-modified Lipid | Poloxamer included during encapsulation process |
|---|---|---|
| 6 | 0.4% | 0.0% |
| 7 | 0.4% | 2% |
| 8 | 0.0% | 2% |

Figure 2:
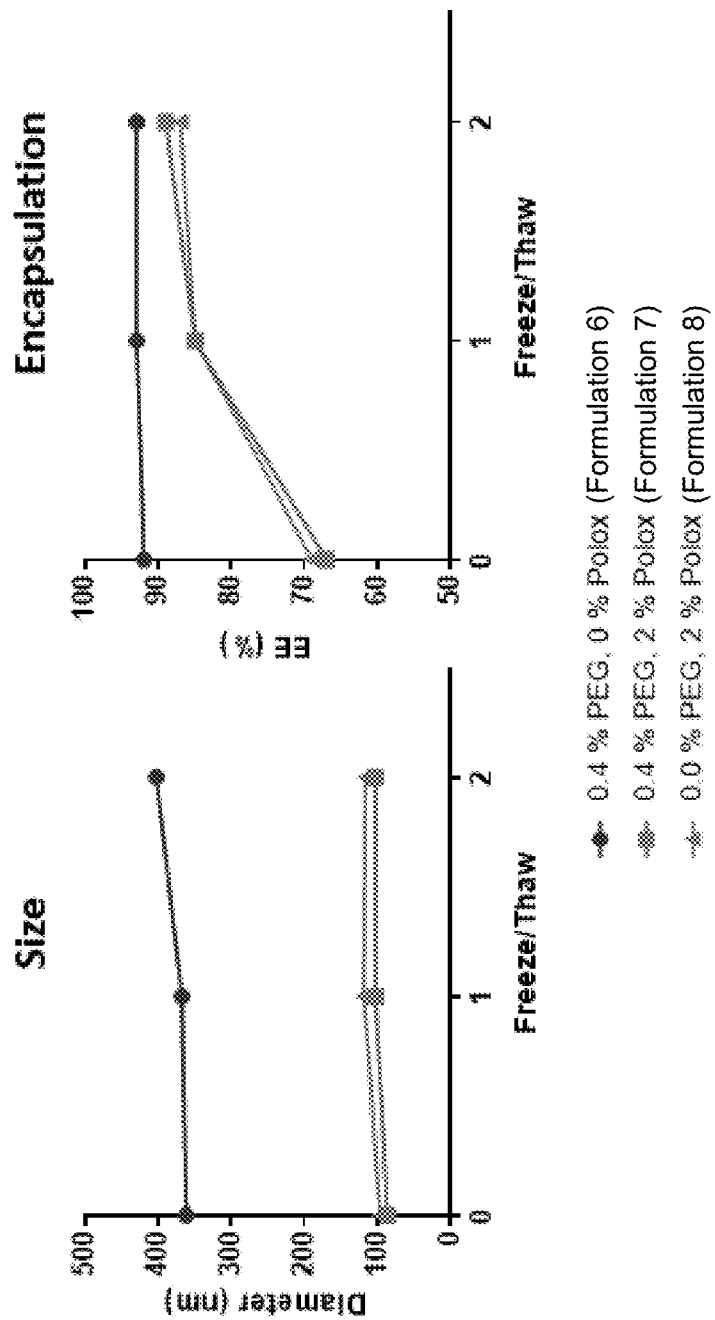
FIG. 2 depicts an exemplary graphical representation of size and encapsulation efficiency of mRNA-LNP formulations shown in Table 3 before and after one or two freeze/thaw cycles.

As shown in FIG. 2, LNP Formulations 7 and 8 containing 0.4% and 0% PEG, respectively, and formed in the presence of 2% poloxamer maintained their average particle sizes of around 100 nm after 2 freeze/thaw cycles. More specifically, the increases of the particle sizes after one and two freeze/thaw cycles appeared to be within 10% of their respective original average sizes. Formulation 6 contains 0.4% PEG and was formed without poloxamer. It had an average particle size of about 370 nm before the freeze/thaw and the average size increased to above 400 nm after two freeze/thaw cycles. More surprisingly, the encapsulation efficiency significantly increased after the first freeze/thaw cycle for Formulations 7 and 8, which included 2% poloxamer during the mRNA-LNP encapsulation process.

Example 4. Formation of mRNA-LNPs with Low or No PEG-Modified Lipid in the Presence of Poloxamer This example further illustrates that mRNA-LNPs with low or no PEG-modified lipids made in the presence of Poloxamer have average sizes and size distributions suitable for therapeutic uses.

Different LNP formulations with varying amounts of PEG-modified lipids and poloxamers, as shown in Table 4, were made by the above-described encapsulation process and analyzed. Notably, same cationic lipid, helper lipid, cholesterol, cholesterol, and mRNA were used to prepare the LNP formulations in this example.

TABLE 4

Exemplary mRNA-LNPs with various amount of PEG-modified lipid and Poloxamer

Figure 3:
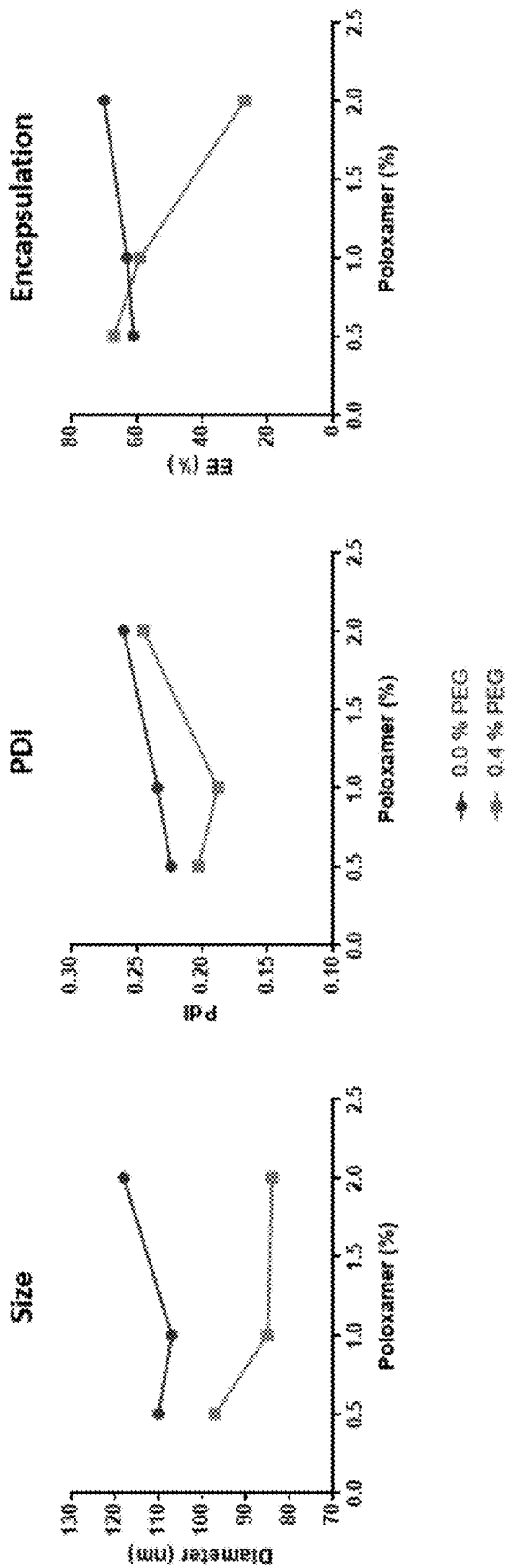
FIG. 3 depicts an exemplary graphical representation of size, PDI and encapsulation efficiency of mRNA-LNP formulations with varying PEG-modified lipid % and poloxamer %, as shown in Table 4.

| Formulation | PEG-modified Lipid | Poloxamer included during encapsulation process |
|---|---|---|
| 9 | 0.0% | 0.5% |
| 10 | 0.0% | 1.0% |
| 11 | 0.0% | 2.0% |
| 12 | 0.4% | 0.5% |
| 13 | 0.4% | 1.0% |
| 14 | 0.4% | 2.0% | mRNA-loaded LNPs were formed in the absence of PEG-modified lipids (Formulations 9-11). This was achieved by adding poloxamer during the encapsulation process as described above. Notably, mRNA-LNPs without PEG-modified lipids were made with a low percent (e.g., 0.5%) of poloxamer (Formulation 9). As shown in FIG. 3, the average sizes of all LNPs containing 0.4% PEG-modified lipids made with varying amount of poloxamer were below 100 nm. The average sizes of all LNPs with no PEG-modified lipids made with varying amount of poloxamer were below 130 nm. The PDIs for all LNPs with or without PEG-modified lipids made with varying amounts of poloxamer were around or below 0.25.

Figure 4:
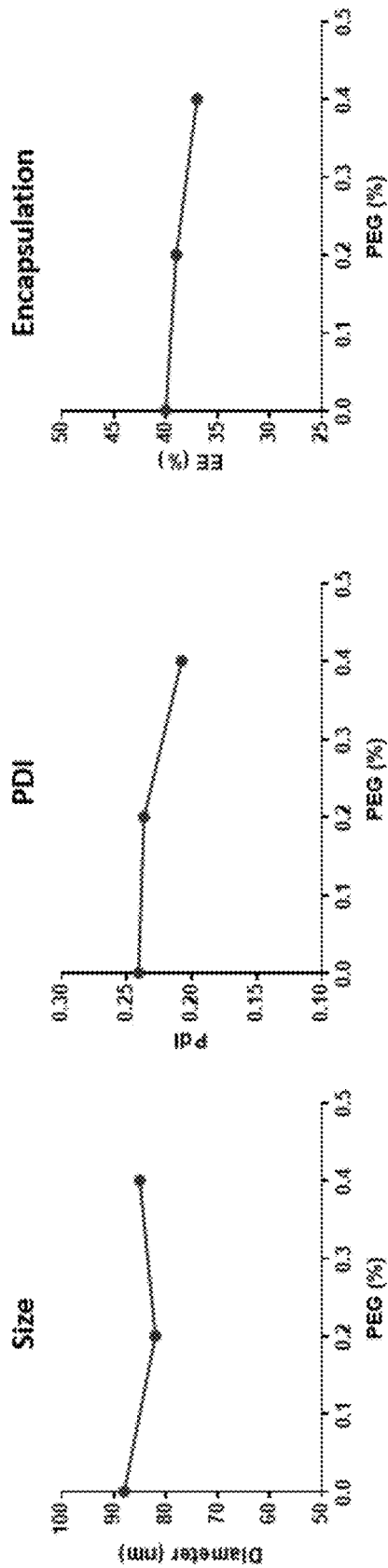
FIG. 4 depicts an exemplary graphical representation of size and encapsulation efficiency of mRNA-LNP formulations with various PEG-modified lipid % and poloxamer, as shown in Table 4.

The effect of % PEG-modified lipids was also tested, as shown in FIG. 4. FIG. 4 shows that mRNA-LNPs were made with very low or no PEG-modified lipids in the presence of poloxamer with average sizes below 100 nm and PDIs below 0.25. As the same lipid components (e.g., cationic lipids, helper lipids, and cholesterol) and the same mRNA were used to prepare the mRNA-LNPs, the changes observed in this example are due to percent changes in the PEG-modified lipids and/or poloxamer.

Example 5. Poloxamer Stabilizes LNPs with Lower Component Systems

This example illustrates that mRNA-LNPs with less than four components can be made according to the present invention and have average sizes suitable for therapeutic uses.

Specifically, mRNA-LNPs with different components (e.g., four, three and two) were made in the presence of poloxamer as described above and characterized. Specific components, average particle sizes, PDIs and encapsulation efficiencies for different formulations were shown in Table 5. Notably, the same lipid components (e.g., cationic lipid, helper lipid, and/or cholesterol), and the same mRNA were used to prepare the LNP formulations in this example.

TABLE 5

LNPs with different components

| Formulation | Number of components | Components | Size (nm) | PDI | Encapsulation Efficiency % |
|---|---|---|---|---|---|
| 16 | Four | Cationic lipid, helper lipid, cholesterol, PEG-modified lipid (No poloxamer) | 87 | 0.184 | 87 |
| 1 | Three | Cationic lipid, helper lipid, cholesterol (+ Poloxamer) | 124 | 0.177 | 54 |
| 17 | Two | Cationic lipid, helper lipid (50:50) (+ Poloxamer) | 113 | 0.185 | 75 |
| 18 | Two | Cationic lipid, helper lipid (25:75) (+ Poloxamer) | 112 | 0.188 | 95 |

As shown in Table 5, mRNA-LNPs were made with three- or two-components when poloxamer was included during the encapsulation process. All have small sizes (e.g., below 125 nm) with acceptable PDI (e.g., below 0.20) and encapsulation efficiency. Remarkably, the two-component LNPs (Formulations 17 and 18), with different cationic to helper lipids ratios, both had small average sizes (less than 120 nm) and high encapsulation efficiency (e.g., >75%).

Example 6. Stable LNPs Substantially Free of PEG-Modified Lipids can be Formed with Different Cationic Lipids and Various Poloxamers This example illustrates that the present invention can be used to produce stable mRNA-LNPs containing various cationic lipids and different mRNAs and substantially free of PEG-modified lipids.

Specifically, as shown in Table 6, mRNA encoding an EPO or FFL protein was encapsulated into LNPs containing different cationic lipids at N/P ratio of 4 in the presence of Poloxamer 407.

TABLE 6 mRNA-LNPs comprising Poloxamer 407 are formed with different cationic lipids and mRNA constructs

| Cationic Lipid | mRNA | Size (nm) | PDI | EE % |
|---|---|---|---|---|
| CCBene | EPO | 97 | 0.143 | 60 |
|  | FFL | 92 | 0.164 | 41 |
| ML-7 | EPO | 114 | 0.166 | 58 |
|  | FFL | 108 | 0.155 | 94 |
| MC-3 | EPO | 93 | 0.156 | 32 |
|  | FFL | 92 | 0.178 |  |
| ML-2 | EPO | 140 | 0.094 | 86 |
|  | FFL | 280 | 0.091 |  |

The results show that stable mRNA-LNPs substantially free of PEG-modified lipids can be formed with various cationic lipids and mRNA constructs. LNPs comprising CCBene, ML-7, and MC3 showed particularly small-sized LNPs of less than 120 nm.

Example 7. Successful In Vivo Expression by Delivery of mRNA-LNPs Formed Using Poloxamer This example demonstrates that administration of mRNA-LNPs formed with poloxamer resulted in successful in vivo protein expression. Particularly, EPO mRNA-loaded LNPs were administered via subcutaneous (SC) and intravenous (IV) routes to CD-1 mice, and the EPO protein expression level was detected in mice liver and serum at 6 and 24 hours post-administration. Four different LNPs with varying amount of PEG-modified lipids and formed with 0.5% poloxamer were tested as shown in Table 7 below. Conventional LNPs with 5% PEG-modified lipids were also administered as controls (Groups B and F shown in Table 7).

TABLE 7

Animal study of mRNA-LNPs comprising poloxamer

| Group | ROA | No. of Animals | Formulation | PEG-modified Lipid | Poloxamer included during encapsulation process | Dose Level (mg/kg) |
|---|---|---|---|---|---|---|
| A | SC | 4 | Saline |  |  | 0.0 |
| B | SC | 4 | 16 | 5.0% | 0.0% | 0.8 |
| C | SC | 4 | 3 | 0.4% | 0.5% | 0.8 |
| D | SC | 4 | 2 | 0.2% | 0.5% | 0.8 |
| E | SC | 4 | 1 | 0.0% | 0.5% | 0.8 |
| F | IV | 4 | 16 | 5.0% | 0.0% | 0.4 |
| G | IV | 4 | 3 | 0.4% | 0.5% | 0.4 |

TABLE 7-continued

Animal study of mRNA-LNPs comprising poloxamer

| Group | ROA | No. of Animals | Formulation | PEG-modified Lipid | Poloxamer included during encapsulation process | Dose Level (mg/kg) |
|---|---|---|---|---|---|---|
| H | IV | 4 | 2 | 0.2% | 0.5% | 0.4 |
| I | IV | 4 | 1 | 0.0% | 0.5% | 0.4 |

Figure 5:
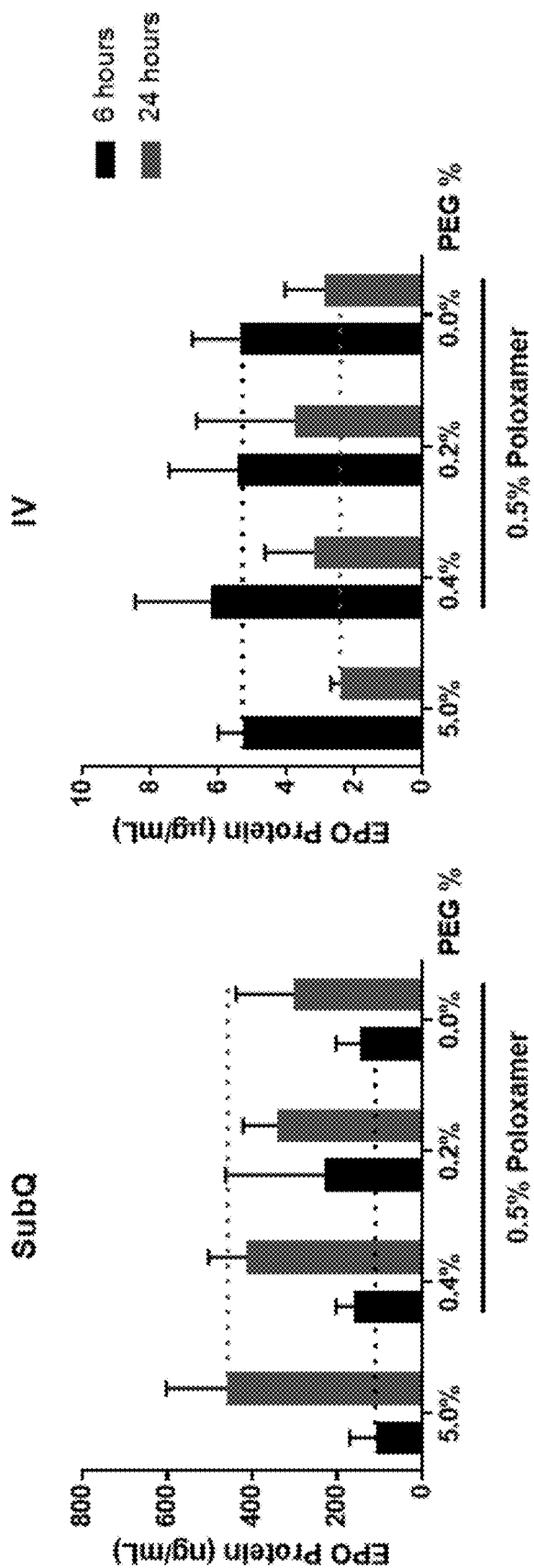
FIG. 5 depicts an exemplary graph of protein levels as measured via ELISA at 6 and 24 hours post administration. The protein detected results from in vivo translation of the mRNA encapsulated in the LNP formulations shown in Table 7, which was delivered by subcutaneous or intravenous administration to mice.

As shown in FIG. 5, poloxamer shielded LNPs with low or no PEG-modified lipids achieved in vivo protein expression profile similar to conventional LNPs (e.g., those with 5% PEG-modified lipids). These data demonstrate that mRNA-LNPs made using poloxamer according to the invention, comprising low (e.g., <0.5%) or no PEG-modified lipids or PEG, can be used successfully for in vivo protein expression for therapeutic purposes.

Example 8. Quantification of Poloxamer in mRNA-LNP Formulations

This example illustrates an exemplary method of quantifying the final concentration of poloxamer in mRNA-LNPs made according to the present invention.

Figure 6B:
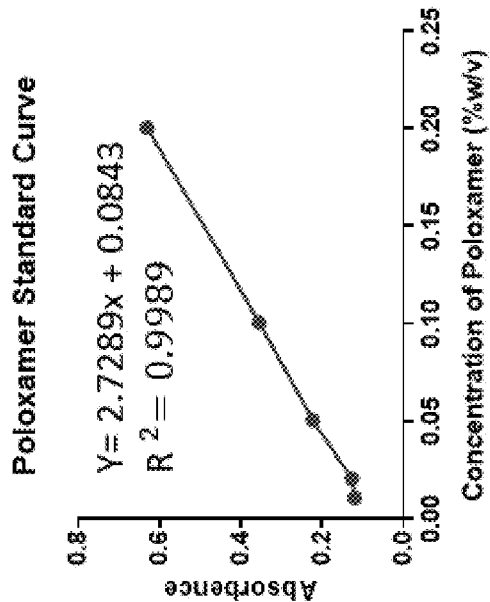
FIGS. 6A and 6B show an exemplary method for quantifying the amount of poloxamer.
Figure 6A:
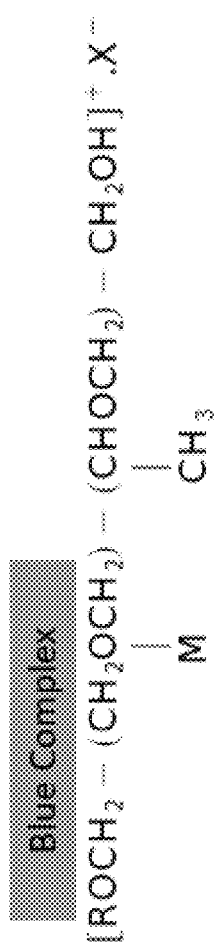

Specifically, this method takes an advantage of the fact that poloxamer competes with cobalt thiocyanate, and forms a blue precipitate as shown in FIG. 6A. After the precipitate is formed, the blue precipitate is dissolved in acetone, and the color intensity, which is directly proportional to poloxamer, is measured at 624 nm wavelength. A standard curve with known concentrations of poloxamer was plotted as shown in FIG. 6B. This standard curve can be used to determine the amount of poloxamer in a given sample.

Example 9. Successful In Vivo Expression of mRNA-LNPs with Various Poloxamers and Non-Cationic Lipids This example illustrates that various poloxamers and non-cationic lipids can be used to produce stable mRNA-LNPs that are substantially free of PEG-modified lipids. This example further demonstrates that administration of mRNA-LNPs formed with poloxamer resulted in successful in vivo protein expression.

Different LNP formulations with various poloxamer and non-cationic lipids, and varying amounts of PEG-modified lipids, as shown in Table 8, were made with cationic lipid cDD-TE4-E12 by the above-described encapsulation process and analyzed. In this particular experiment, mRNA encoding OTC (ornithine transcarbamylase) was encapsulated.

TABLE 8

Exemplary mRNA-LNPs with various components

Figure 7:
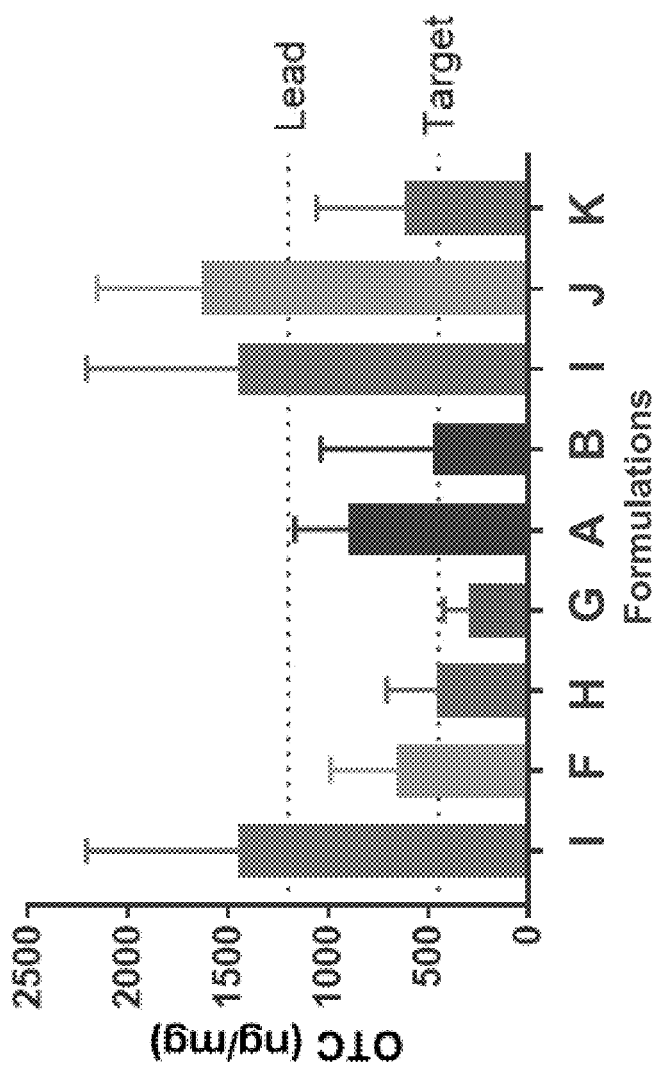
FIG. 7 depicts an exemplary graph of OTC protein levels as measured via ELISA at 24 hours post administration. The protein detected results from in vivo translation of the mRNA encapsulated in the LNP formulations shown in Table 8, which was delivered by intravenous administration to mice.

| Formulation | Poloxamer (Pluronic) | Ratio (PEG:Cationic lipid:cholesterol:non-cationic lipid) | Non-cationic lipid | Size (nm) | PDI | EE % |
|---|---|---|---|---|---|---|
| A | P-234 (P-84) | 0.5:40:27.5:32 | DOPE | 95 | 0.075 | 100 |
| B | P-407 (F127) | 0.5:40:27.5:32 | DOPE | 87 | 0.134 | 87 |
| C | P-234 (P-84) | 0:40:28:32 | DOPE | Crashed | | |
| D | P-407 (F127) | 0:40:28:32 | DOPE | 92 | 0.152 | 89 |
| E | P-338 (P108) | 0:40:28:32 | DOPE | 97 | 0.146 | Low |
| F | P-234 (P-84) | 0.5:40:27.5:32 | DEPE | 125 | 0.080 | 100 |
| G | P-407 (F127) | 0.5:40:27.5:32 | DEPE | 133 | 0.140 | 99 |
| H | P-338 (P108) | 0.5:40:27.5:32 | DEPE | 126 | 0.090 | 99 |
| I | No Poloxamer | 3:40:25:32 | DEPE | | | |
| J | No Poloxamer | 2:40:26:32 | DEPE | | | |
| K | No Poloxamer | 1.5:40:26.5:32 | DOPE | | | | mRNA-loaded LNPs were formed in the absence or with very low (e.g. 0.5%) of PEG-modified lipids (Formulations A-H). This was achieved by adding poloxamer during the encapsulation process as described above. Various poloxamers and non-cationic lipids can be used to optimize the encapsulation process. The average sizes of all LNPs made in this example were about or below 130 nm, with PDI of about or less than 0.15 and encapsulation efficiency of about or greater than 90%. As controls, mRNA-loaded LNPs were prepared without poloxamers with varying ratios of PEG-modified lipids (Formulations I-K).

mRNA-LNP formulations comprising OTC mRNA in Table 8 were administered via intravenous (IV) route to mice, and the OTC protein expression level was measured. As shown in FIG. 7, poloxamer shielded LNPs with low PEG-modified lipids achieved in vivo protein expression of about or higher the target expression level. These data demonstrate that mRNA-LNPs with low or no PEG-modified lipids, made using various poloxamers and non-cationic lipids, can be used successfully for in vivo protein expression for therapeutic purposes. Formulations I and J achieved higher potency than Formulations A-H with poloxamers.

EQUIVALENTS

Those skilled in the art will recognize or be able to ascertain using no more than routine experimentation, many equivalents to the specific embodiments of the invention described herein. The scope of the present invention is not intended to be limited to the above Description, but rather is as set forth in the following claims:

We claim:

1. A stable composition comprising lipid nanoparticles encapsulating messenger RNA (mRNA), wherein the mRNA encodes a protein or a peptide, wherein each of the lipid nanoparticles comprises one or more cationic lipids, one or more non-cationic lipids, an amphiphilic block co-polymer, and less than 0.5% of PEG-modified lipids or PEG, and wherein the lipid nanoparticles encapsulating mRNA comprise 0.5% or less of the amphiphilic block co-polymer.

2. The stable composition of claim 1, wherein each of the lipid nanoparticles comprises one cationic lipid, dioleoylphosphatidylethanolamine (DOPE), and less than about 0.5% of PEG-modified lipids or PEG.

3. The stable composition of claim 1, wherein the lipid nanoparticles encapsulating the mRNA maintain an average diameter within 50% of the original average size following one or more freeze thaw cycles.

4. The stable composition of claim 1, wherein the lipid nanoparticles encapsulating the mRNA maintain an average diameter within 5% of the original average size following one or more freeze thaw cycles.

5. The stable composition of claim 1, wherein the lipid nanoparticles have an mRNA encapsulation efficiency of between about 50% and 99%.

6. The stable composition of claim 1, wherein each of the lipid nanoparticles further comprises a cholesterol-based lipid.

7. The stable composition of claim 1, wherein each of the lipid nanoparticles comprises 0.4% of PEG-modified lipids or less, 0.3% of PEG-modified lipids or less, 0.2% of PEG-modified lipids or less, or 0.1% of PEG-modified lipids or less.

8. The stable composition of claim 1, wherein each of the lipid nanoparticles is free of PEG-modified lipids.

9. The stable composition of claim 1, wherein the amphiphilic block copolymer is a poloxamer.

10. A stable composition comprising lipid nanoparticles encapsulating a messenger RNA (mRNA) that encodes a protein or a peptide, wherein each of the lipid nanoparticles comprises one or more cationic lipids, one or more non-cationic lipids, a poloxamer, and is free of PEG-modified lipids or PEG, and wherein the lipid nanoparticles encapsulating the mRNA comprise less than 0.1% of the poloxamer.

11. The stable composition of claim 10, wherein the lipid nanoparticles encapsulating the mRNA generate low to no anti-PEG antibodies, and/or reduce accelerated blood clearance (ABC).

12. A method for delivery of messenger RNA (mRNA) for in vivo production of a protein or a peptide, comprising administering to a subject the composition according to claim 1.

13. The method according to claim 12, wherein administering the composition to the subject does not result in generating anti-PEG antibodies and/or accelerated blood clearance (ABC) in the subject.

14. A process of encapsulating messenger RNA (mRNA) in lipid nanoparticles comprising:
   a) mixing an mRNA solution and a lipid solution comprising one or more cationic lipids, one or more non-cationic lipids, and less than 0.5% of PEG-modified lipids or PEG in the presence of 0.5% or less of a poloxamer; and
   b) removing the poloxamer from the mixture.

15. The process of claim 14, wherein the lipid solution comprises 0.4% of PEG-modified lipids or less, 0.3% of PEG-modified lipids or less, 0.2% of PEG-modified lipids or less, 0.1% of PEG-modified lipids or less, or free of PEG modified lipid or PEG.

16. The process of claim 14, wherein the poloxamer is removed by dialysis.

\* \* \* \* \*